(12) United States Patent
Coe

(10) Patent No.: US 8,670,865 B2
(45) Date of Patent: *Mar. 11, 2014

(54) INTERACTIVE MEDICINE ORGANIZER

(75) Inventor: Matthew Coe, Annandale, NJ (US)

(73) Assignee: One World DMG, Ltd., Warren, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/238,097

(22) Filed: Sep. 21, 2011

(65) Prior Publication Data

US 2012/0006847 A1    Jan. 12, 2012

Related U.S. Application Data

(63) Continuation-in-part of application No. 12/802,015, filed on May 27, 2010, now Pat. No. 8,195,330.

(60) Provisional application No. 61/217,608, filed on Jun. 2, 2009.

(51) Int. Cl.
*G06F 17/00* (2006.01)

(52) U.S. Cl.
USPC ........... 700/243; 700/240; 700/242; 700/244; 700/232

(58) Field of Classification Search
USPC .......... 700/231, 232, 236, 242–243, 240, 244
See application file for complete search history.

(56) References Cited

U.S. PATENT DOCUMENTS

| | | | |
|---|---|---|---|
| 6,507,275 B2 | 1/2003 | Romano et al. | |
| 7,147,127 B2 | 12/2006 | Lepke et al. | |
| 7,182,218 B2 | 2/2007 | Raines | |
| 7,735,681 B2 * | 6/2010 | Handfeld et al. | 221/152 |
| 8,140,185 B2 * | 3/2012 | Simmons et al. | 700/241 |
| 8,195,330 B2 * | 6/2012 | Coe | 700/243 |
| 2002/0000917 A1 | 1/2002 | Rubenstein | |
| 2007/0185615 A1 * | 8/2007 | Bossi et al. | 700/244 |
| 2008/0033594 A1 * | 2/2008 | Packes et al. | 700/232 |
| 2008/0119958 A1 | 5/2008 | Bear et al. | |
| 2008/0300719 A1 * | 12/2008 | Duke | 700/244 |
| 2009/0057328 A1 * | 3/2009 | Ratnakar | 221/1 |
| 2009/0281657 A1 * | 11/2009 | Gak et al. | 700/242 |
| 2010/0305749 A1 * | 12/2010 | Coe | 700/231 |
| 2011/0060457 A1 * | 3/2011 | De Vrught et al. | 700/241 |

OTHER PUBLICATIONS

U.S. Appl. No. 12/802,015, Coe.

* cited by examiner

*Primary Examiner* — Michael K Collins
(74) *Attorney, Agent, or Firm* — Mitchell J. Mehlman, Esq.

(57) ABSTRACT

Interactive medicine organizers and methods comprising integrated software and hardware elements and multifunctional interactive wireless devices to provide assistance to individuals who need to organize or monitor the administration of one or more medications are provided.

20 Claims, 25 Drawing Sheets

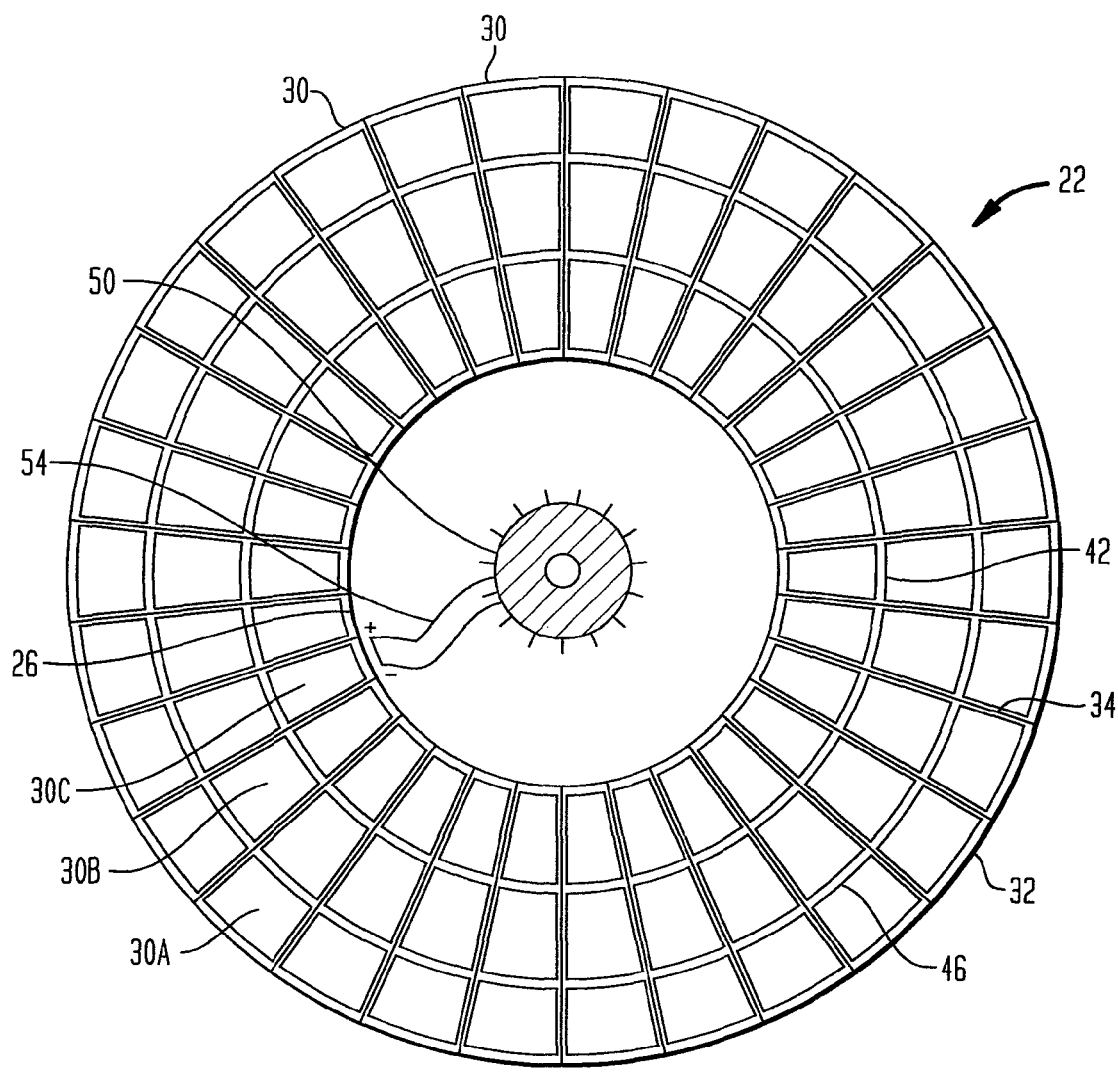

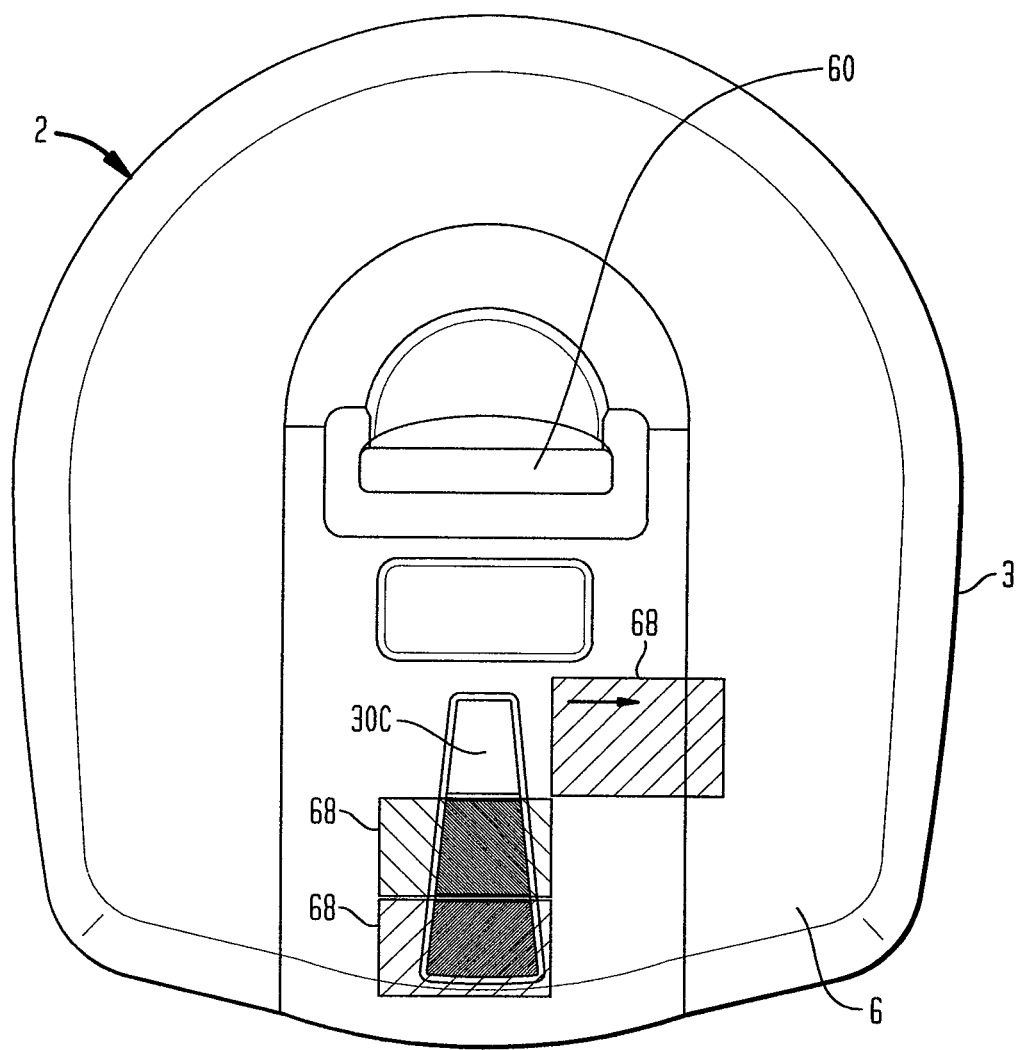

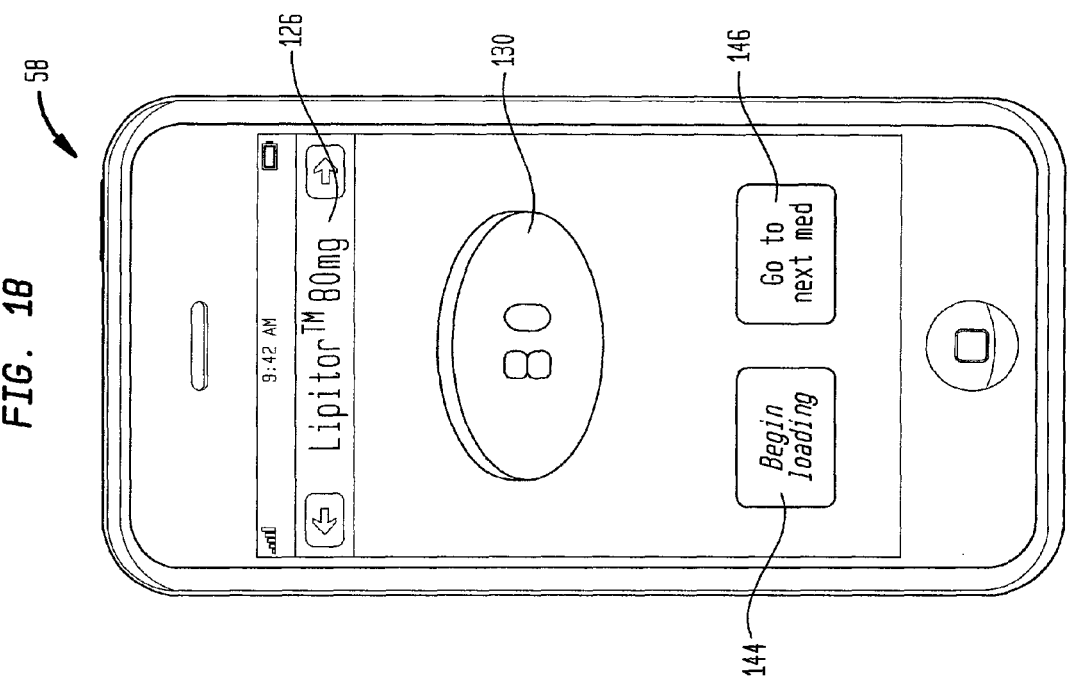
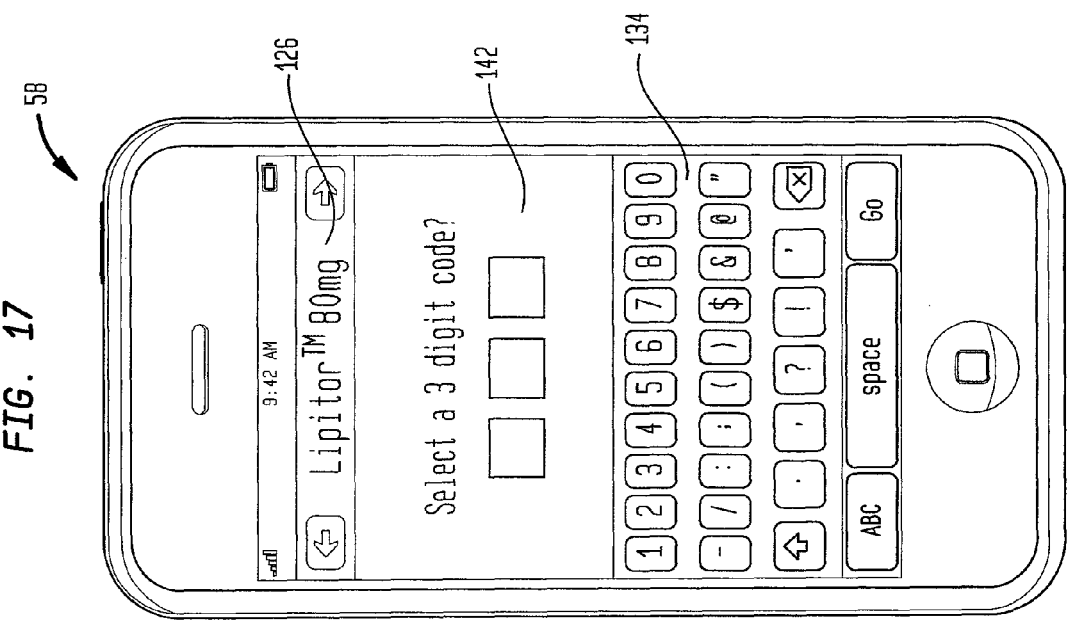

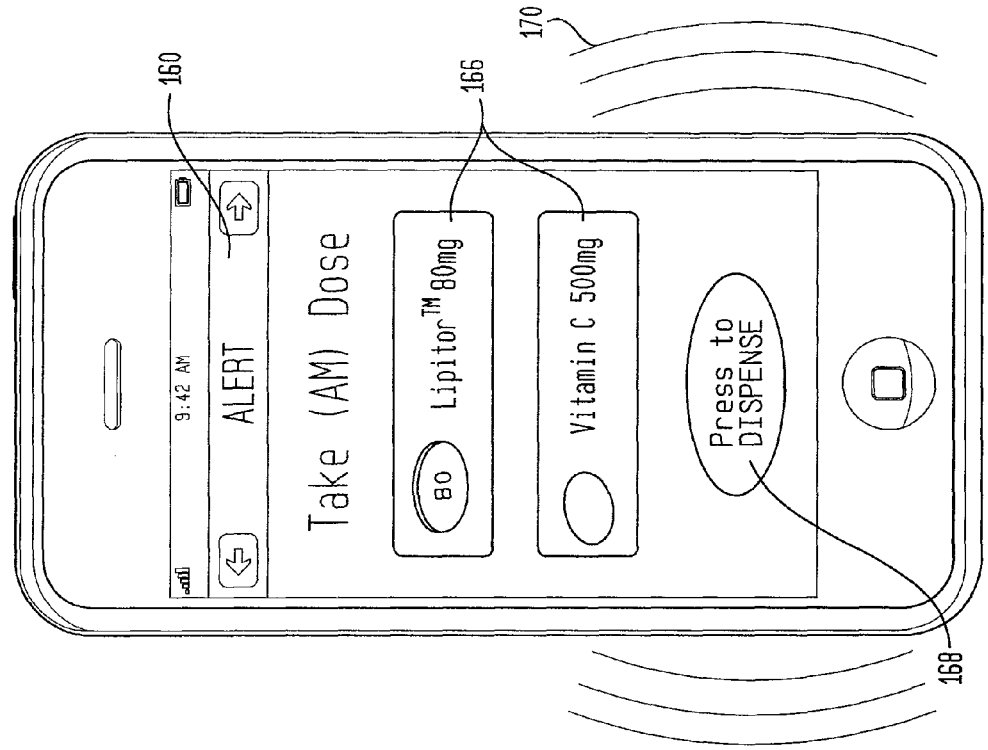
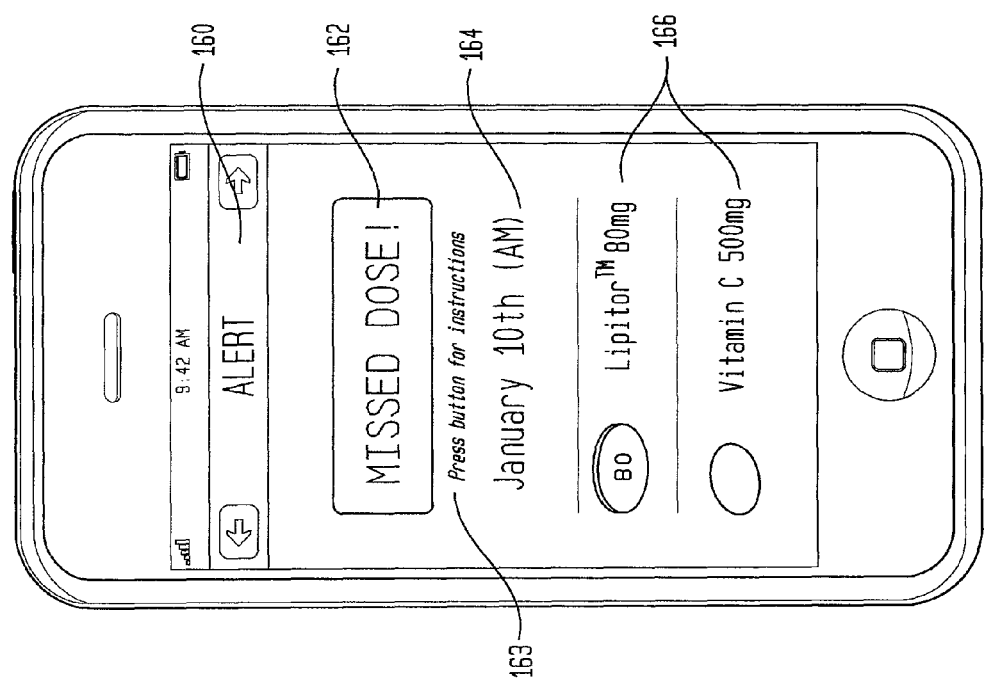

INTERACTIVE MEDICINE ORGANIZER

CROSS-REFERENCE TO RELATED APPLICATION

This application is a continuation-in-part of non-provisional application Ser. No. 12/802,015, entitled "INTERACTIVE MEDICINE ORGANIZER", filed on May 27, 2010 now U.S. Pat. No. 8,195,330, which claims priority to Provisional Application Ser. No. 61/217,608, titled "INTERACTIVE MEDICINE ORGANIZER", filed Jun. 2, 2009, the disclosure of which is incorporated herein by reference in its entirety.

BACKGROUND OF THE INVENTION

The present invention relates to interactive medicine organizers (IMOs) including multifunctional interactive wireless devices that can communicate with one or more dispensers to dispense medications and methods for monitoring and increasing patient compliance with regard to timely dispensing of medications or dietary supplements.

Many people take one or more medications or dietary supplements, such as minerals or vitamins, several times a day to maintain or improve their health. Often, these medications or supplements must be taken at specific times each day. If medications or supplements are not taken at the proper times, individual health may be jeopardized. For example, failure to take a prescribed medication for treatment of heart disease can result in severe health consequences such as a heart attack or stroke. Similarly, patients that seek to take extra doses before the prescribed time interval can be in danger of an overdose. Non-compliance with a prescribed dose regimen includes patients who fail to take a dose at a prescribed time or patients who take one or more extra doses that are not in compliance with the minimum time between dose of the particular prescription or label instructions for ingestion.

Further, non-compliance with a prescribed regimen of one or more medications, particularly in the elderly and the aging population of "baby boomers", can result in billions of dollars of unnecessary health care costs.

Many people who take one or more medication or supplement a day are able to take medications or supplements without assistance. However, many people who take one or more medication or supplement a day require a reminder or the assistance of a care taker. Care takers may be one or more members of the patient's family or other individuals, such as friends, nurses, nurse's aids and the like. It can be difficult for a patient or a care taker to organize a patient's medications or supplements to insure compliance with a predetermined schedule. Further, it can be extremely difficult to monitor compliance with multiple medication schedules. Failure to properly monitor compliance can result in catastrophic health consequences to the patient and high levels of care taker anxiety, which can also lead to increased health problems for care takers.

Known pill organizers have severe limitations. One such limitation is the need to remind the patient to take their medication when the patient is away from the dispensing unit. Another such limitation is the inability for a user or a care taker to remotely monitor a patient's compliance with a medication schedule.

The present invention solves these difficult problems in a novel manner by improving the overall ease of compliance with a programmable schedule for dispensing one or more medications or supplements. Rather than requiring, for example, a dedicated alarm unit that the patient must carry with them, the instant invention is more efficient because many people already carry multifunctional interactive wireless devices (MIWDs) such as cell phones.

Interactive medicine organizers comprising multifunctional interactive wireless devices such as cell phones having programmable software that can communicate with one or more medicine dispensers and methods for monitoring and improving patient compliance with medication schedules are disclosed herein.

SUMMARY OF THE INVENTION

In one aspect of the invention an apparatus comprises a dispenser body. The body has a housing. A loading door can be connected to the housing. A tray can have one or more chambers, the tray can be connected to the housing. A dispensing door can be connected to the housing. A docking station can be connected to the housing. A multifunctional interactive wireless device can be capable of i) docking with the docking station, ii) commanding the tray to a plurality of positions, iii) commanding the loading door to a plurality of positions and iv) commanding the dispensing door to a plurality of positions. The device can execute a software application for determining a plurality of positions of the tray, the loading door, and the dispensing door based on a data set input by a user.

In one embodiment, the tray can be substantially circular.

In another embodiment, the tray can have thirty chambers.

In yet other embodiments, each of the thirty chambers can be divided into a plurality of compartments.

In some embodiments, each of the thirty chambers can be divided into three compartments.

In other embodiments, the tray can have seven chambers.

In yet other embodiments, each of the seven chambers can be divided into a plurality of compartments.

In certain embodiments, each of said seven chambers can be divided into three compartments.

In certain embodiments the multifunctional interactive wireless device is an iPhone™.

In other embodiments, the data set comprises a name of a pill; a strength of the pill; and a time schedule for dispensing the pill.

In some embodiments, the multifunctional interactive wireless device communicates an alarm to a user. The alarm can be based on a time schedule.

In still other embodiments, the multifunctional interactive wireless device can communicate a signal to a remote database. The signal indicates whether or not the contents of one or more chambers have been dispensed.

In another aspect of the present invention a method comprises 1) entering a data set into a software application. The application can be executed on a multifunctional interactive wireless device; 2) loading one or more pills into a tray. The tray can have one or more chambers; 3) docking the multifunctional interactive wireless device with a docking station; and 4) commanding a dispensing door to dispense one or more pills.

In one embodiment of this aspect, the data set comprises a name of one of more pills; a strength of the one or more pills; and a time that the one or more pills are to be dispensed.

Another embodiment comprises the step of transmitting a signal from the multifunctional interactive wireless device to a remote database. The signal can indicate either a confirmation of dispensing the one or more pills or a failure to dispense the one or more pills.

In yet another embodiment the method comprises the step of transmitting an alarm from the multifunctional interactive wireless device. The alarm can be transmitted when the one or more pills are not dispensed within a predetermined time of a scheduled dispense time.

In certain embodiments, the multifunctional interactive wireless device is an iPhone.

In some embodiments the method comprises the step of sending a signal to the remote database when a user attempts to dispense one or more pills before a predetermined time.

In certain other embodiments, the method comprises the step of locking the dispensing door when a user attempts to dispense one or more pills before a predetermined time.

In yet another aspect of the invention a system for managing patient compliance with a medication schedule comprises a multifunctional interactive wireless device having a microprocessor; a storage means for storing data on a storage medium; an arithmetic circuit configured to prepare said storage means to magnetically store selected data on said storage medium; an arithmetic logic circuit configured to retrieve information from an input file, calculate a tray position and send a signal to a motor to effectuate said tray position; an arithmetic logic circuit configured to retrieve information from an input file, calculate a dispensing door position and send a signal to a motor to effectuate said door position; an arithmetic logic circuit configured to retrieve information from an input file, calculate an alarm condition and send a signal to a effectuate said alarm condition; an arithmetic logic circuit configured to retrieve information from an input file, calculate a dispensed condition or an undispensed condition and send a signal to a server to record said dispensed condition or said undispensed condition; an arithmetic logic circuit configured to retrieve information from an input file, calculate a dispense history and display a signal indicating said dispense history for monitoring compliance with a medication schedule.

BRIEF DESCRIPTION OF THE DRAWINGS

FIG. 4A is a plan view of some of the elements included in the interactive medicine organizer of FIG. 1 showing a tray and motor configuration.

FIG. 4D is a plan view of some of the elements included in the interactive medicine organizer of FIG. 1 showing a third loading configuration.

FIG. 17 is an isometric view of a MIWD included in the interactive medicine organizer of FIG. 1 showing a screen for entering security data.

FIG. 18 is an isometric view of a MIWD included in the interactive medicine organizer of FIG. 1 showing a screen for selecting a next medication or loading option.

FIG. 23 is an isometric view of a MIWD included in the interactive medicine organizer of FIG. 1 showing a screen indicating an alert for a missed dose.

FIG. 24 is an isometric view of a MIWD included in the interactive medicine organizer of FIG. 1 showing a screen for dispensing medications.

DETAILED DESCRIPTION

As used herein, the terms pill and pills refer to any size or shape of a capsule, caplet, granule, tablet, lozenge, suppository, ampoule or any other dosage form typically used for oral nasal, dermal or rectal administration of a medication or dietary supplement or for rectal administration in the form of a suppository. The term pill or pills can include medications used for injections. The terms pill and pills may also include delivery forms typically used for topical administration, such as encapsulated and packaged liquid suspensions or emulsions, powders, creams, salves, serums, ointments and the like. The terms pill, medicine or medication may be singular or plural and are used interchangeably herein.

As used herein, the terms pill, medicine and or medication refer to prescription and over-the-counter medications, dietary supplements such as vitamins, minerals or cosmetic products. Further, the terms pill, medicine and or medication refer to any product in pill form which the user has a need or desire to use on a predetermined, scheduled basis.

Figure 3:
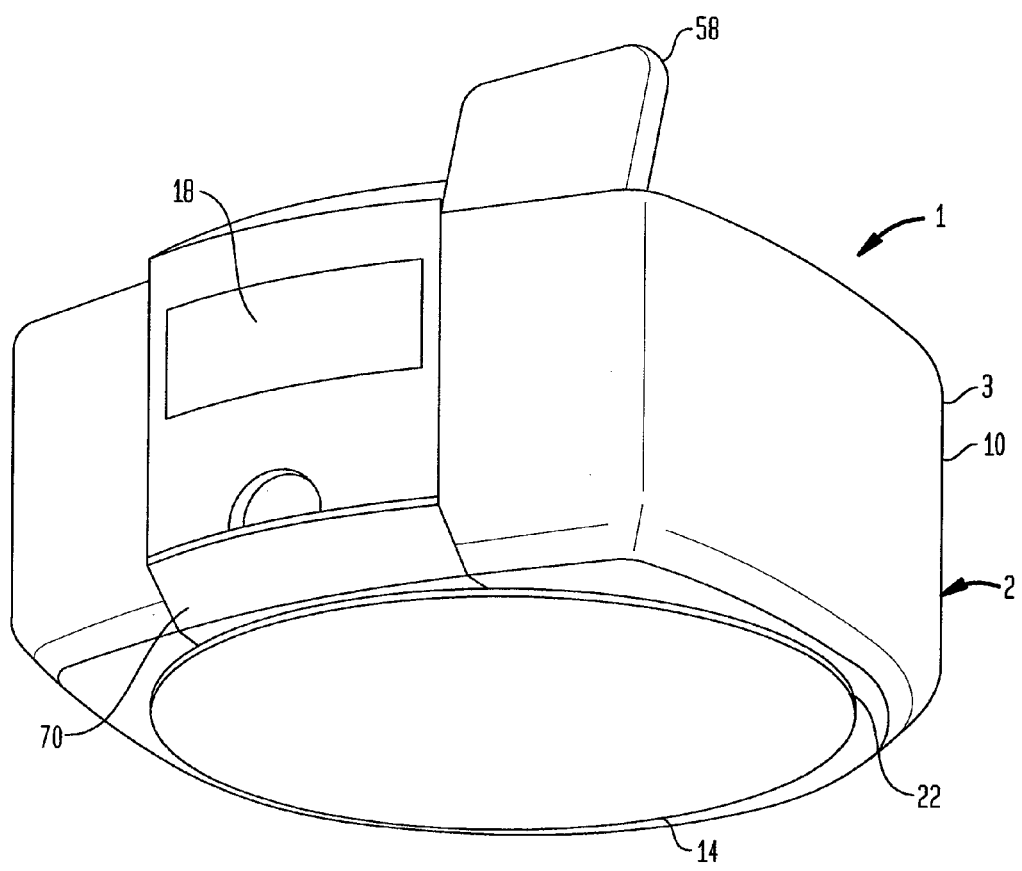
FIG. 3 is an isometric view of some of the elements included in the interactive medicine organizer of FIG. 1.

As shown in FIGS. 1-4E, interactive medicine organizer (IMO) 1 in accordance with one embodiment of the present invention includes a dispenser body 2 having a housing 3. Housing 3 has a top surface 6, side surface 10 and bottom surface 14 (FIG. 3). Housing 3 can be fabricated from plastics or other structural materials which will be known to one skilled in the art of manufacturing.

In this embodiment, an LED clock 18 is mounted to housing 3. The clock 18 can be used as a home clock or as an alarm clock. The clock 18 can also indicate, for example, the time of day, the day of the week, the date or other time related data. Clock 18 can be selected from any type of clock including digital LED devices or any other type of clock well known in the arts.

As shown in FIG. 4A, tray 22 can be rotatably mounted within housing 3. In this embodiment, tray 22 is circularly shaped and comprises thirty (30) "daily" chambers 30, each having an inner wall 26 an outer wall 32 and side walls 34. Each daily chamber 30 is subdivided into three compartments 30A, 30B and 30C bounded by walls 26, 42, 46 and 32, respectively. Each of compartments 30A, 30B and 30C is capable of storing one or more pills. A plurality of tray geometries, chamber configurations, and compartment configurations are contemplated within the scope of the present invention. For example, a weekly tray having seven (7) daily chambers and twenty one (21) corresponding compartments is contemplated.

To facilitate loading, compartments 30A, 30B, 30C can be color coded, for example, to indicate a first color for a morning dose, a second color for an afternoon dose and a third color for an evening dose. Tray 22 can be molded or fabricated from any suitable durable structural material, for example, a polymeric material. Suitable materials and manufacturing methods will be well known to those skilled in the art.

In this particular embodiment, tray 22 is designed to hold a thirty (30) day supply of all the pills that a patient takes in a thirty day period. In this way, three doses a day are available to the patient for about a month. Each compartment can hold thirty (30) or more pills, depending on the size of the pills, thereby allowing the user to load about nine hundred pills or more into a single tray 22.

Tray 22 is indexed and controlled by electric motor 50 (FIG. 4A). Motor 50 is mechanically connected to tray 22 and electrically connected to an AC power source (not shown) through leads 54. Motor 50 is commanded by electrical signals generated by a microprocessor (not shown) in multifunctional interactive wireless device (MIWD) 58. An MIWD can be, for example, an iPhone™, a BlackBerry™, a Centro™, a PDA, an iPod™, a Droid™, or any similar touch or smart wireless or phone device. Standard motors, such as precision stepper motors, which are known to those of ordinary skill in the art can be utilized to accomplish the movement of any mechanism in the IMO that requires control or movement.

The IMO 1 can include a battery backup system (not shown) to maintain power in the event of an AC power interruption. If power is lost, all data can be stored in the MIWD (58).

Figure 1:
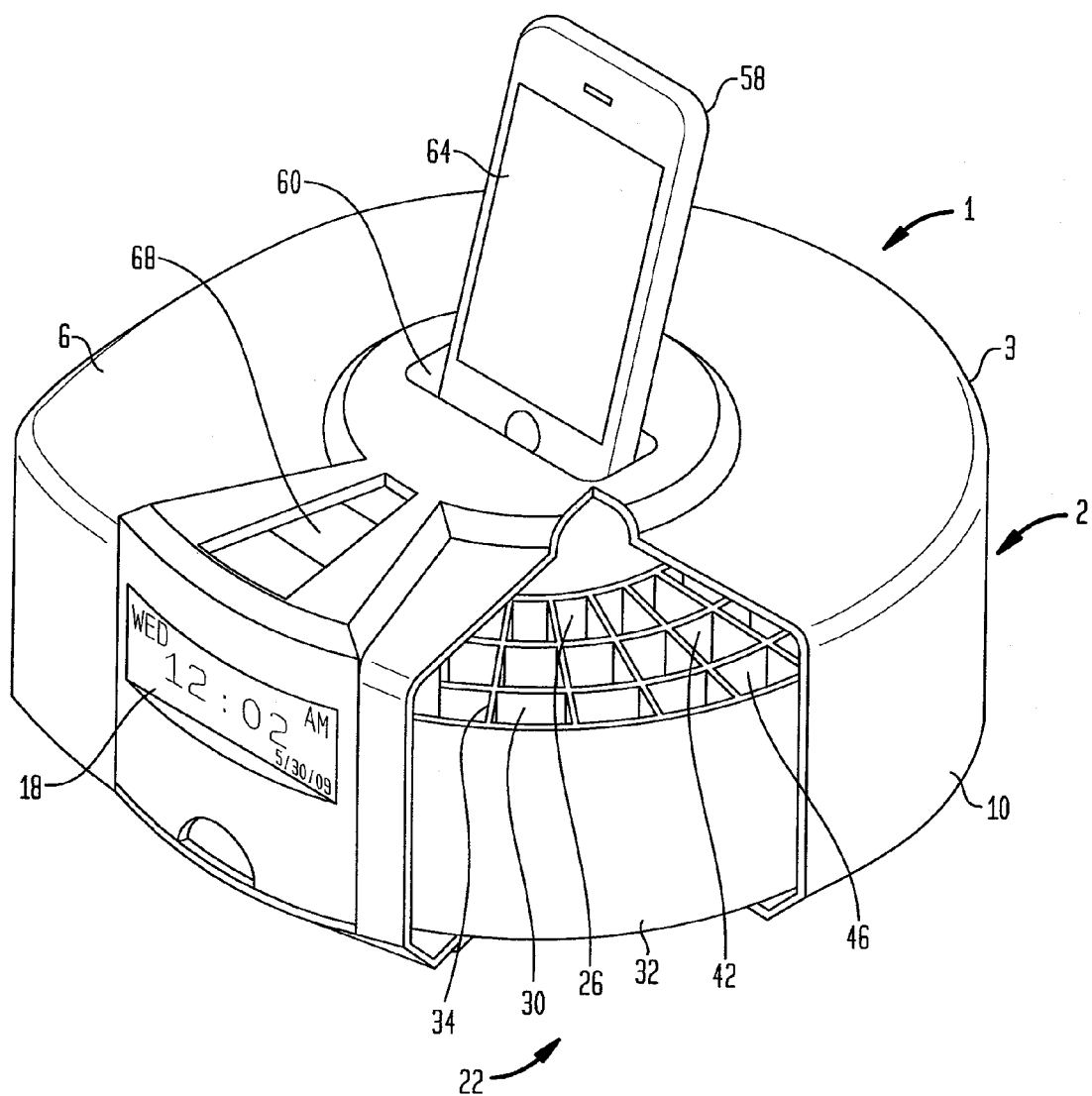
FIG. 1 is an isometric cut away view of an interactive medicine organizer according to one embodiment of the present invention in a dispensing position.
Figure 2:
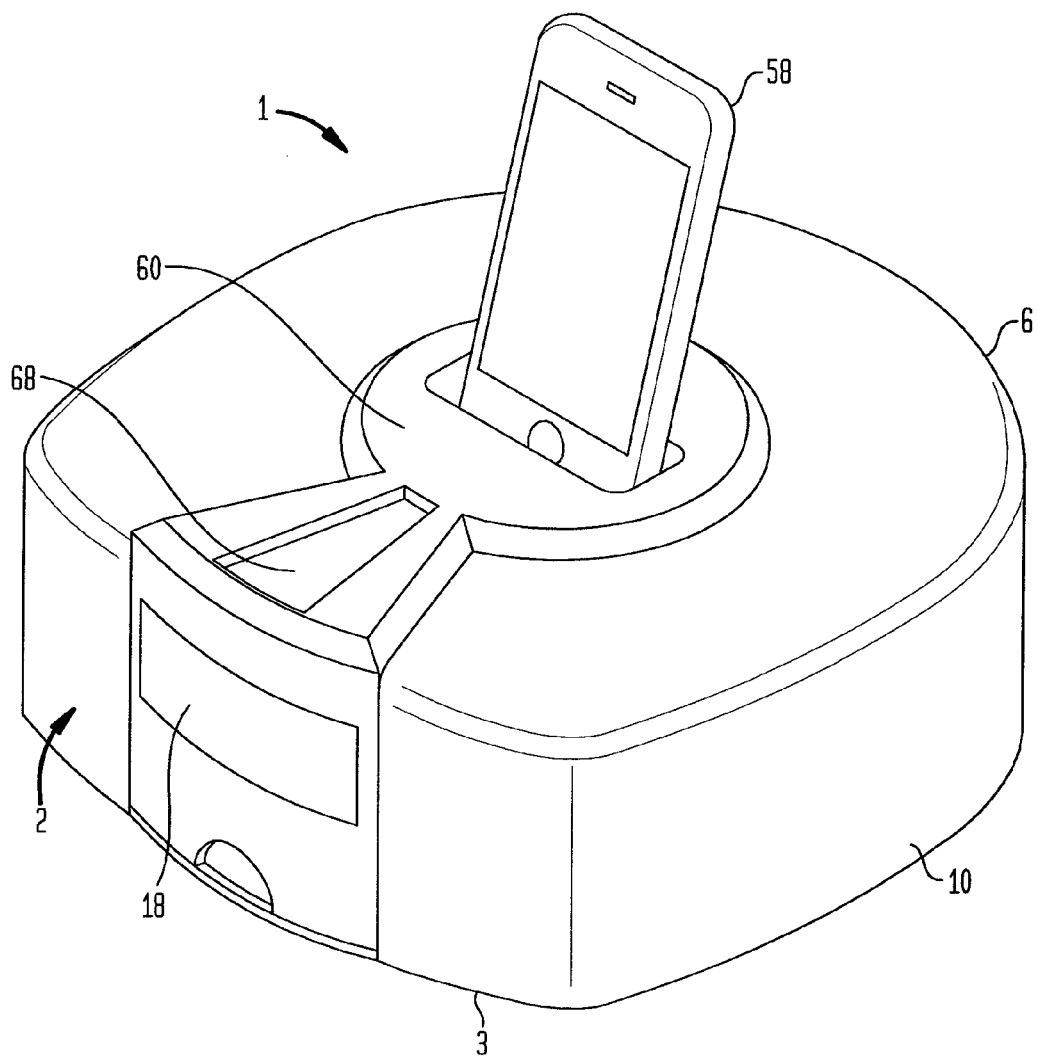
FIG. 2 is an isometric view of some of the elements included in the interactive medicine organizer of FIG. 1.
Figure 4:
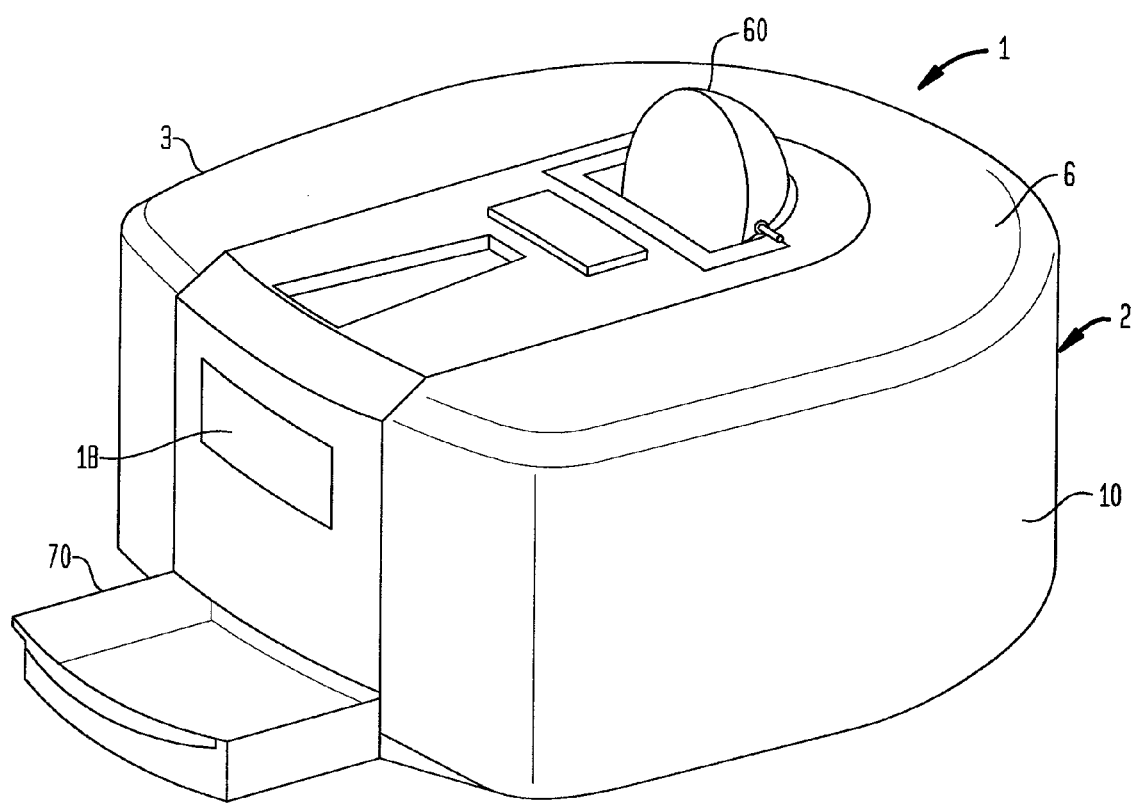
FIG. 4 is an isometric view of some of the elements included in the interactive medicine organizer of FIG. 1 showing a dispensing drawer in an open position.
Figure 4B:
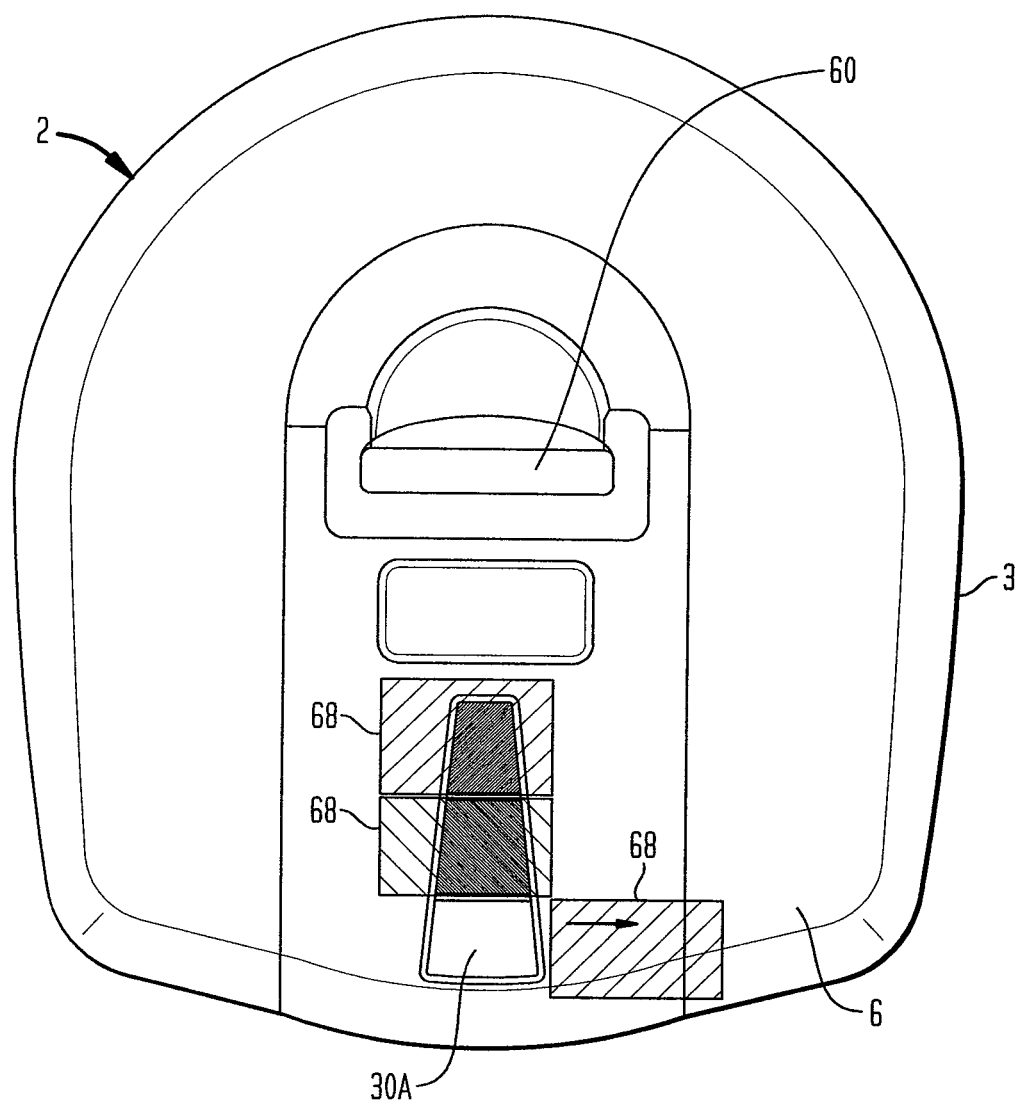
FIG. 4B is a plan view of some of the elements included in the interactive medicine organizer of FIG. 1 showing one loading configuration.
Figure 4C:
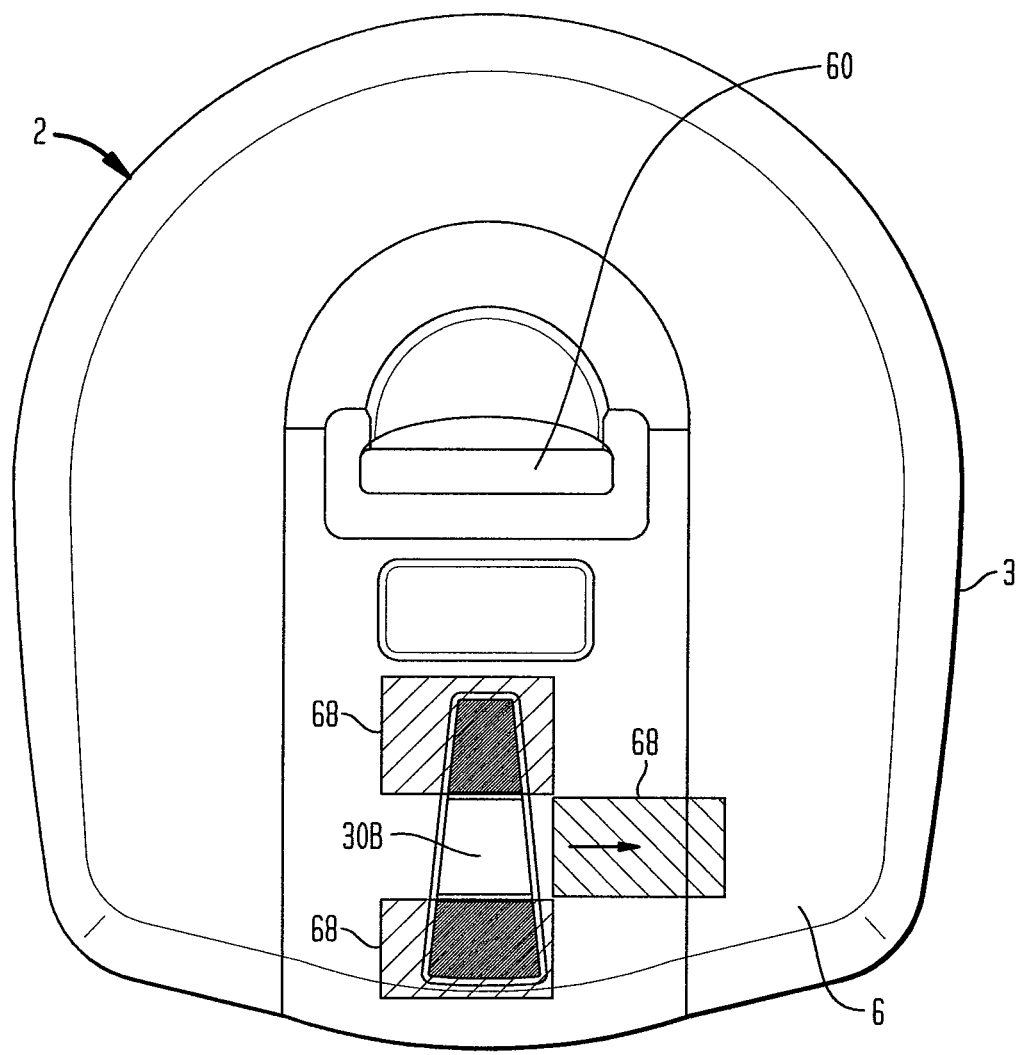
FIG. 4C is a plan view of some of the elements included in the interactive medicine organizer of FIG. 1 showing a second loading configuration.
Figure 4E:
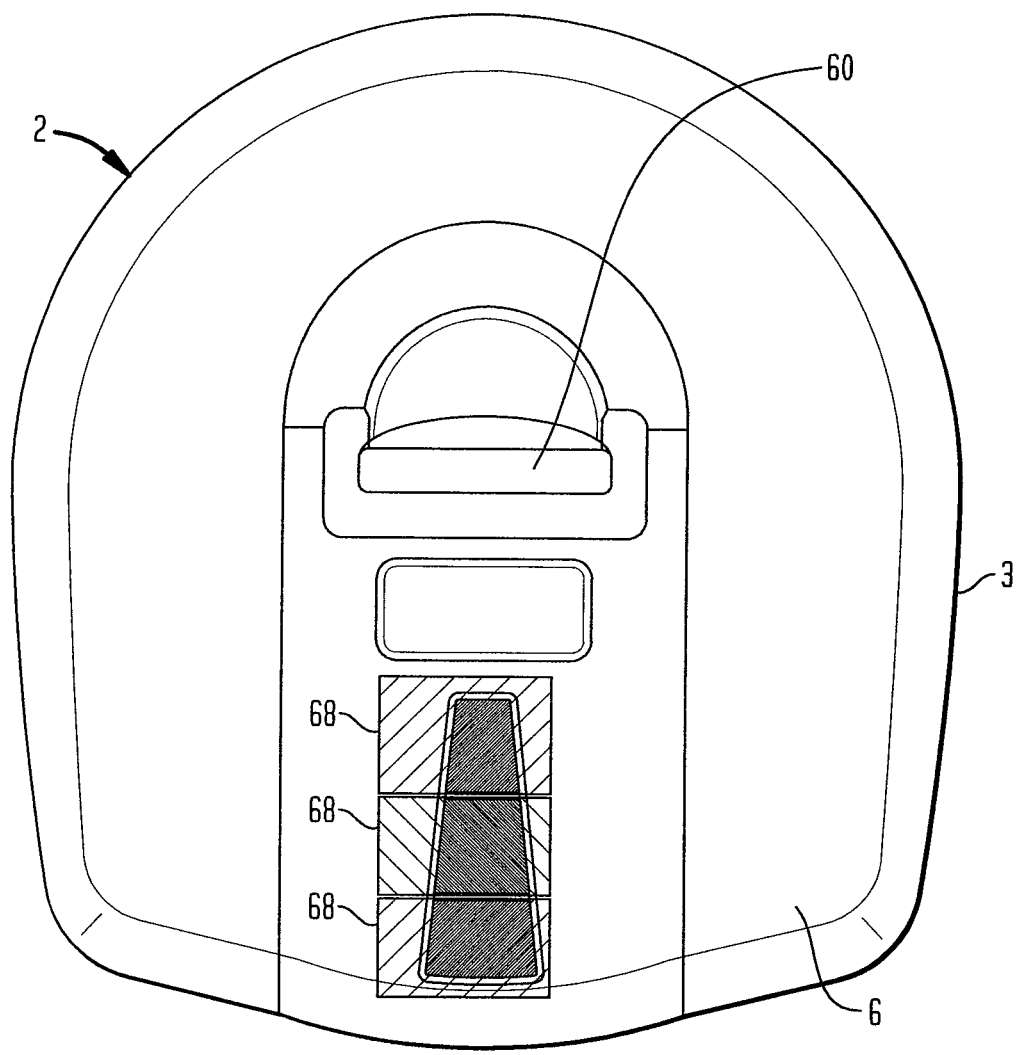
FIG. 4E is a plan view of some of the elements included in the interactive medicine organizer of FIG. 1 showing a closed configuration.

The IMO 1 further includes a docking station 60. Docking station 60 is connected to top surface 6 of housing 3. Docking station 60 is adapted to accept and connect to MIWD 58. Docking station 60 provides mechanical means to support the MIWD such that pressing on a touch screen 64 incorporated in the MIWD will not damage the IMO and will facilitate durable mechanical and electrical connectivity between MIWD 58 and dispenser body 2 (FIGS. 1, 4). The MIWD 58 mates with the docking station 60 such that the MIWD may be electrically charged or recharged through the AC power source or battery. It will be appreciated that in certain embodiments docking station 60 can comprise a wireless receiver that receives wireless signals from the MIWD and a wireless transmitter that sends wireless signals to the MIWD. In such embodiments, physical docking of the MIWD may not be necessary.

When MIWD 58 is mated to dispenser body 2 through docking station 60, MIWD 58 can send commands to cause electric motor 50 to move. Further, MIWD 58 can receive signals from the motor in order to recognize the position of tray 22 within body 2 such that the position of each compartment 30 may be commanded to any position by motor 50, thus facilitating loading or release of pills from any predetermined compartment. It will be understood that docking station 60 can include any number of adapters such that different types of MIWD can be docked. Such docking adapters and command and control algorithms between electromechanical devices are well known to those of ordinary skill in the art.

Dispenser body 2 incorporates movable loading doors 68 for loading pills into compartments 30A, 30B and 30C. As shown in FIGS. 4B-4E, loading doors 68 can be commanded by the MIWD to an open position for loading each of the compartments 30A, 30B, 30C. Each compartment can correspond with a particular dosage time frame. For example, compartment 30A can be opened for an A.M. dose (FIG. 4B), compartment 30B can be opened for a NOON dose (FIG. 4C), and compartment 30C can be opened for a P.M. dose (FIG. 4D).

Loading doors 68 can be commanded to a closed or dispensing position (FIG. 4E) in order to protect the contents of the compartments and to ensure that only the desired compartment is loaded. The loading doors are closed when the IMO is not being loaded. The loading doors can be made of a transparent material such that the contents of the compartments aligned with the loading doors are visible to the user. The loading door configuration can include other commandable mechanisms such as, for example, a rotating member with apertures spaced to facilitate an open position in which at least one compartment can be loaded or a closed position in which all compartments are closed and cannot be loaded.

In certain embodiments, the IMO includes a single loading door that overlies the housing. The door can be connected to the housing by a hinge. In operation, the loading door can be opened to expose the tray and loading compartments for loading pills. The door can be commanded by the MIWD to an open loading position or a closed or locked position.

Dispenser body 2 further includes movable dispensing doors (not shown). The dispensing doors underlie tray 22 and can operate essentially the same as the loading doors previously described.

Movement of the loading doors or the dispensing doors can be accomplished by commands sent from the MIWD. Door movement can be accomplished by any suitable mechanical system such as a motor and actuator configured to move doors to a desired position. The means for opening and closing loading or dispensing doors will be well known to a person of ordinary skill in the electro-mechanical arts. Any suitable mechanism is contemplated herein.

Drawer 70 (FIGS. 3, 4) underlies tray 22 such that when tray 22 is loaded with pills, and the proper compartment 30 is aligned over drawer 70, the MIWD 58 commands the dispensing doors to a position which allows a specific compartment to open, thus allowing the contents of any compartment (30A, 30B, 30C) to move into drawer 70. Drawer 70 can be slidably connected to housing 3 such that the user may slide drawer 70 to an open position to remove the pills and slide drawer 70 to a closed position to dispense the pills. Drawer 70 can be removed for ease of cleaning or for dispensing pills.

In operation, the IMO is controlled by a software application executed by MIWD 58. In this embodiment, the MIWD is an iPhone™, but any mobile phone or wireless device capable of running third party applications and controlling hardware can also be used. The MIWD 58 can also maintain a wireless internet connection such as, for example, 3G or WiFi technology that allows for connection to the internet. The wireless connection permits, among other things, remote monitoring of a patient's user defined medicine schedule and monitoring compliance with the schedule as will be described further below.

The user interface can have a graphical display designed for ease of use. The user can be guided through a series of steps to set up and program the IMO, dispense pills and perform other desirable functions.

Programming Example

Figure 5:
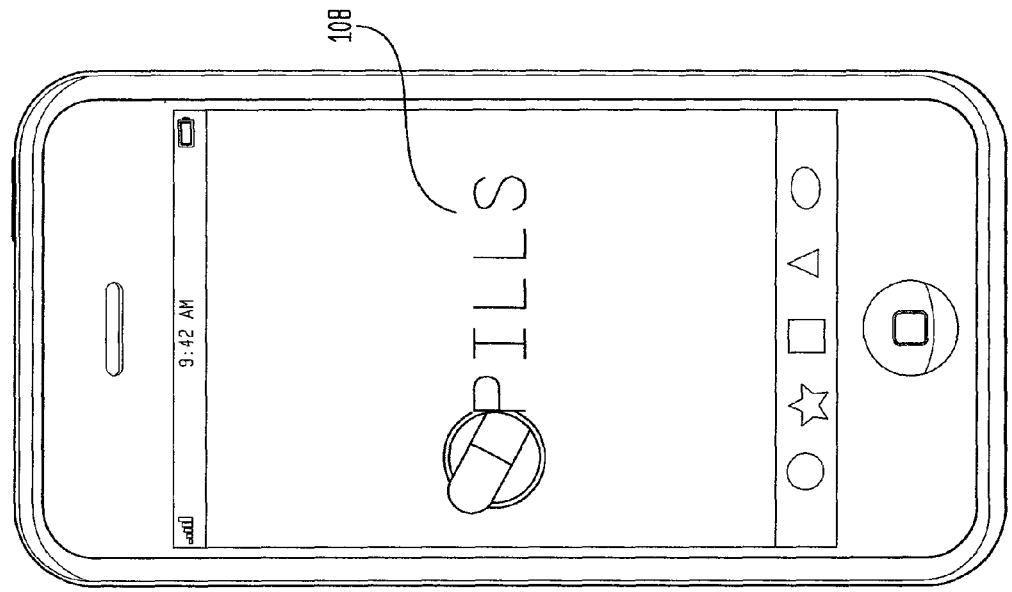
FIG. 5 is an isometric view of a MIWD included in the interactive medicine organizer of FIG. 1 showing a home screen for accessing the organizer software application.
Figure 6:
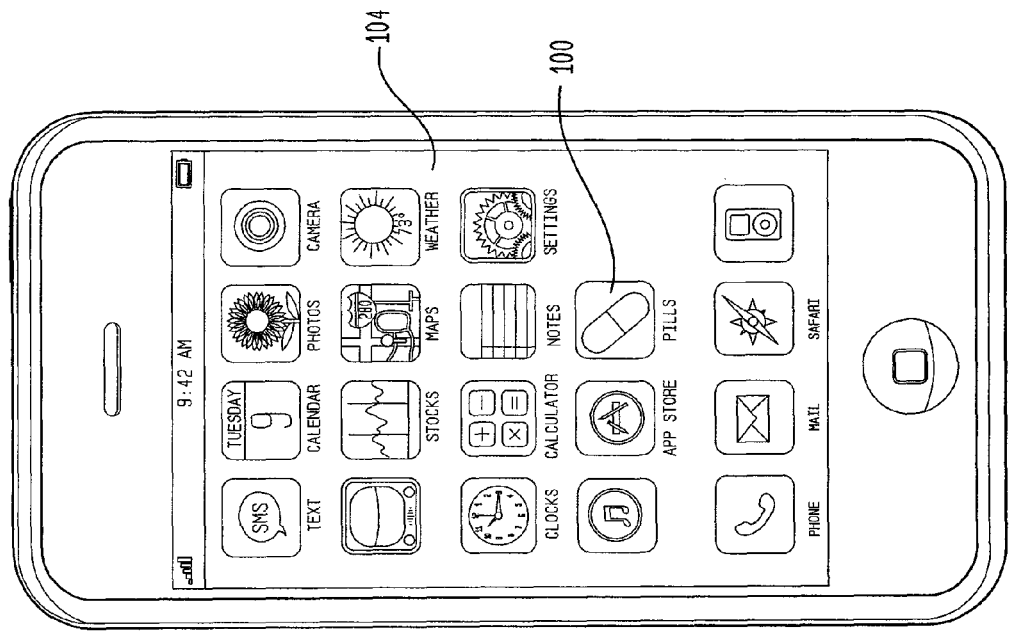
FIG. 6 is an isometric view of a MIWD included in the interactive medicine organizer of FIG. 1 showing a start up screen for accessing the organizer software application.
Figure 7:
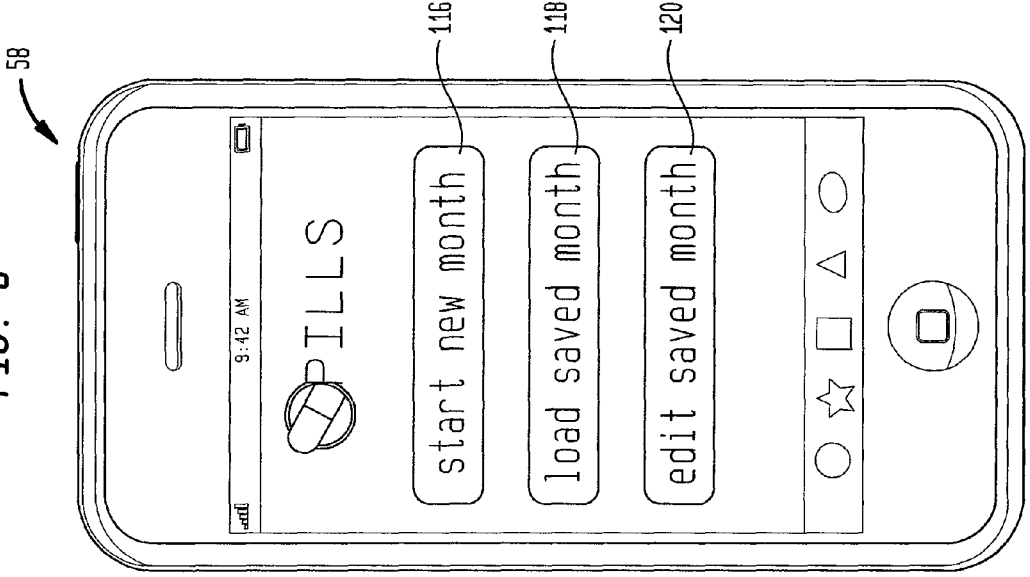
FIG. 7 is an isometric view of a MIWD included in the interactive medicine organizer of FIG. 1 showing user name, password and new user screen for accessing the organizer software application.

In one embodiment, the user can depress an icon 100 on the touch screen homepage 104 of the MIWD 58. The icon identifies the pill dispenser application (FIG. 5). When the application is loaded on the MIWD, an application identification screen, for example, "Pills" 108 is displayed (FIG. 6). Next, the user can be presented with options to enter a user name and password or set up a new user account as depicted in FIG. 7. In the event that the user is a new user 114 or desires to open a new account the user is prompted to enter a user name 110 and password 112. A secure online account can be created for each user on a remote server and linked to the MIWD by a wireless network. In the event that the user already has an account, a secure link will be created to access the user's account on a remote server.

Figure 8:
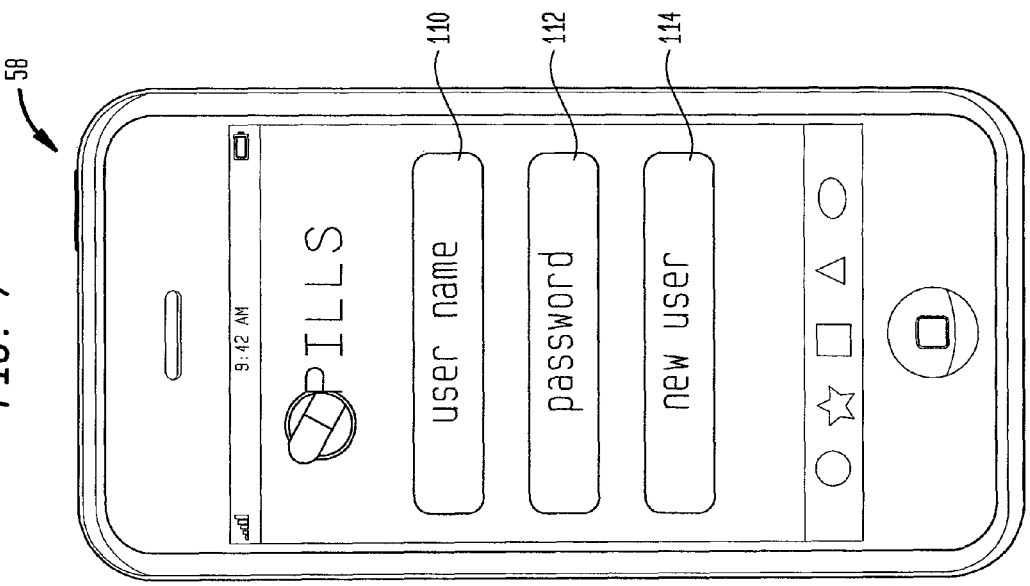
FIG. 8 is an isometric view of a MIWD included in the interactive medicine organizer of FIG. 1 showing a screen for staring, loading or editing a monthly schedule.
Figure 10:
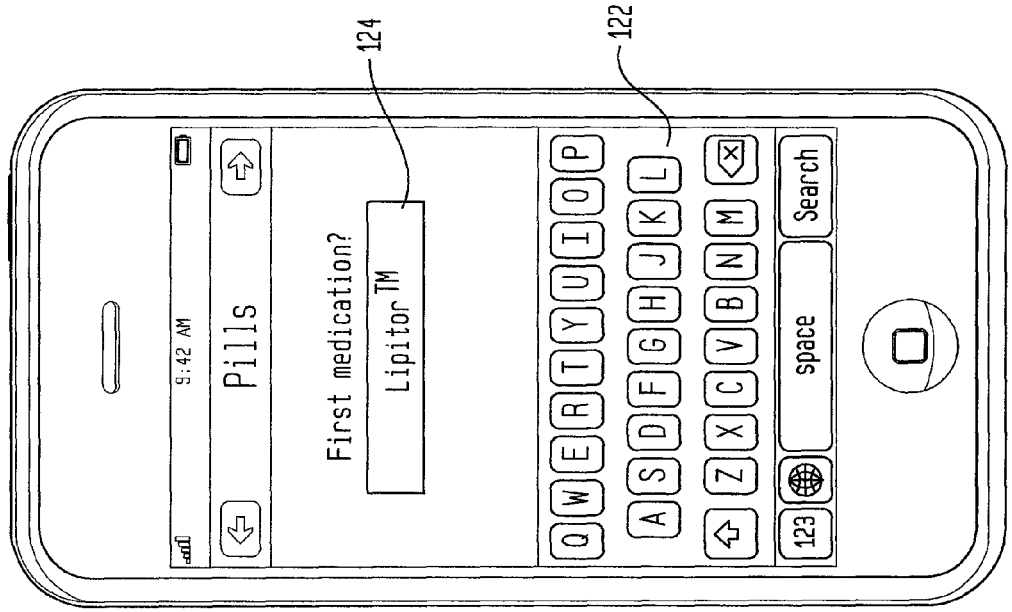
FIG. 10 is an isometric view of a MIWD included in the interactive medicine organizer of FIG. 1 showing a screen for entering first medication name data using a virtual keyboard.
Figure 9:
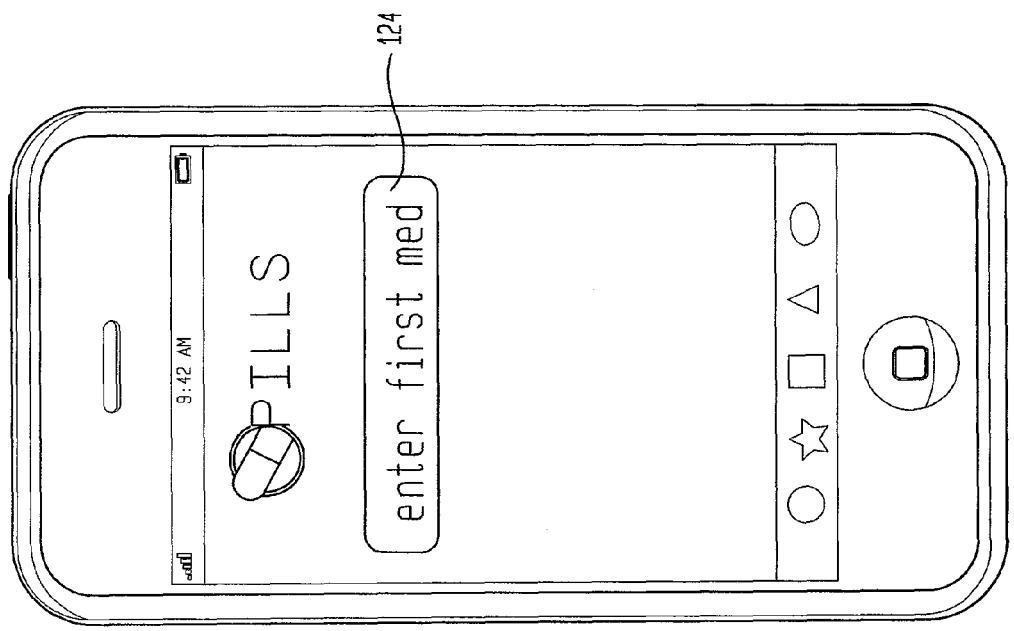
FIG. 9 is an isometric view of a MIWD included in the interactive medicine organizer of FIG. 1 showing a screen for entering first medication data.
Figure 11:
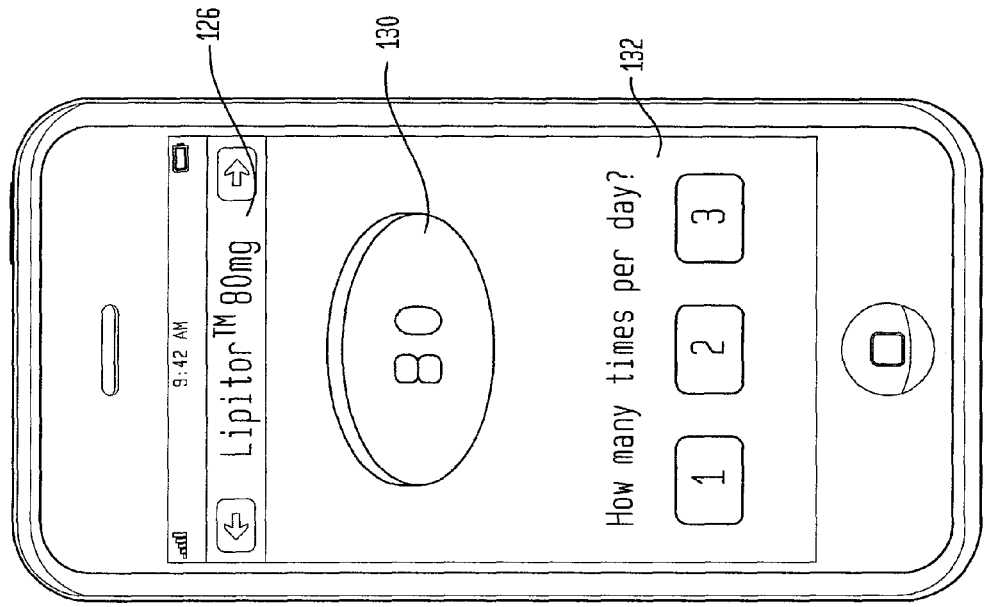
FIG. 11 is an isometric view of a MIWD included in the interactive medicine organizer of FIG. 1 showing a screen for entering first medication strength data.
Figure 12:
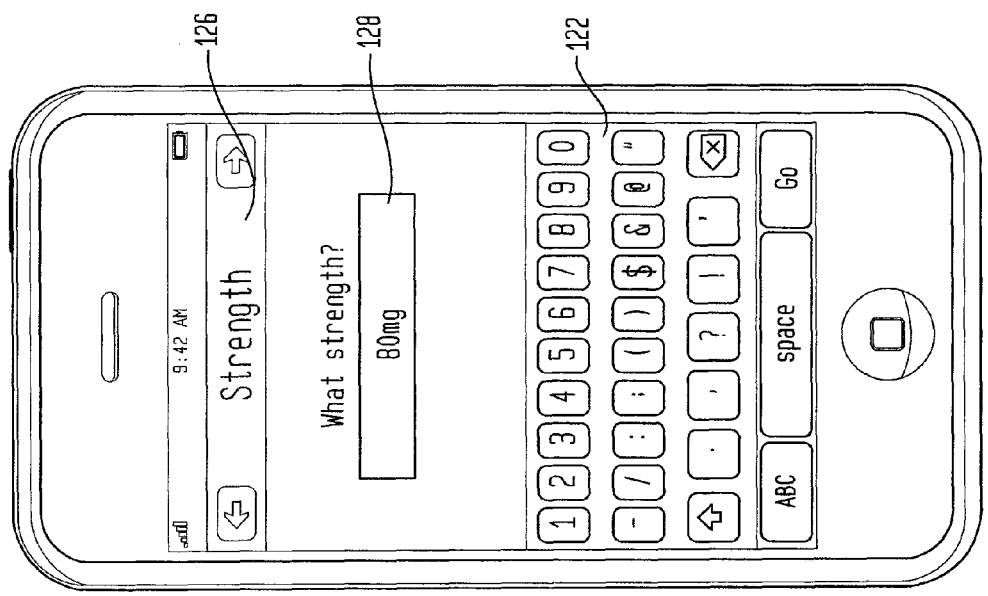
FIG. 12 is an isometric view of a MIWD included in the interactive medicine organizer of FIG. 1 showing a screen for entering first medication times per day data.
Figure 13:
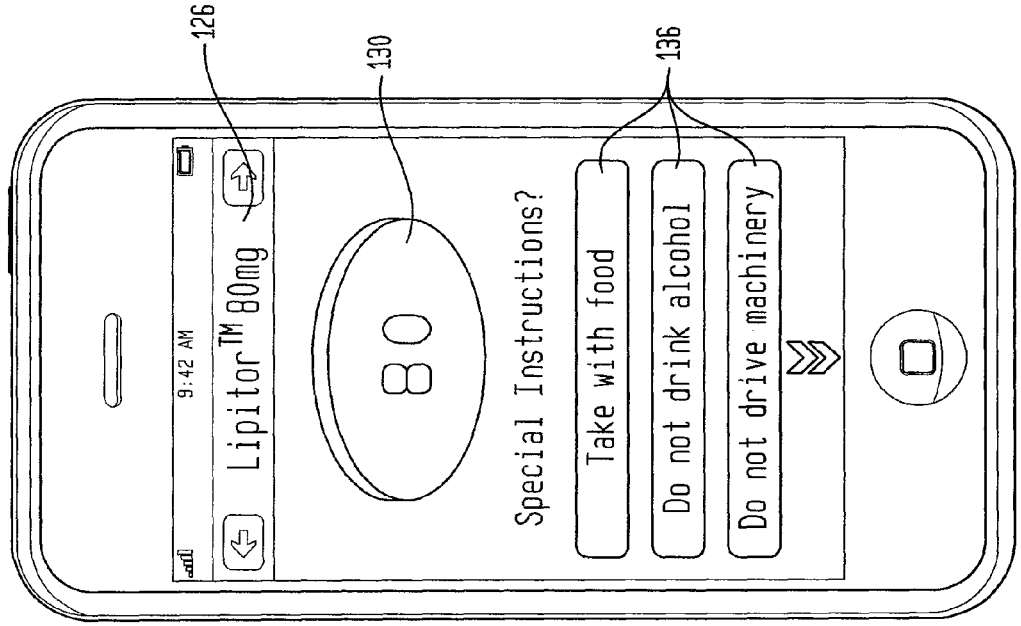
FIG. 13 is an isometric view of a MIWD included in the interactive medicine organizer of FIG. 1 showing a screen for entering first medication time of day data.

As shown in FIG. 8, the user can perform one of several operations such as "start new month" 116, "load saved month" (118) or "edit saved month" 120. If the user is a first time user, the user can select "start new month" 116. The user can then enter each medication that requires dispensing. A mini-keyboard 122 can be used to type in the name of the first medication 124 (FIGS. 9, 10). Next, the user will be prompted to enter the strength 126, or dose size 128 of the medication, for example, 80 mg (FIG. 11). Once the medication name and strength or dose size is entered, subsequent screens can include a graphic depiction 130 of the actual pills (FIGS. 12, 13).

After the user enters the medicine name and strength, the user can be prompted to enter the number of times the medicine is taken per day 132, for example 1, 2, or 3, and the times of day that the medicine is to be taken 134, for example, A.M., NOON, or P.M. (FIGS. 12, 13).

Figure 14:
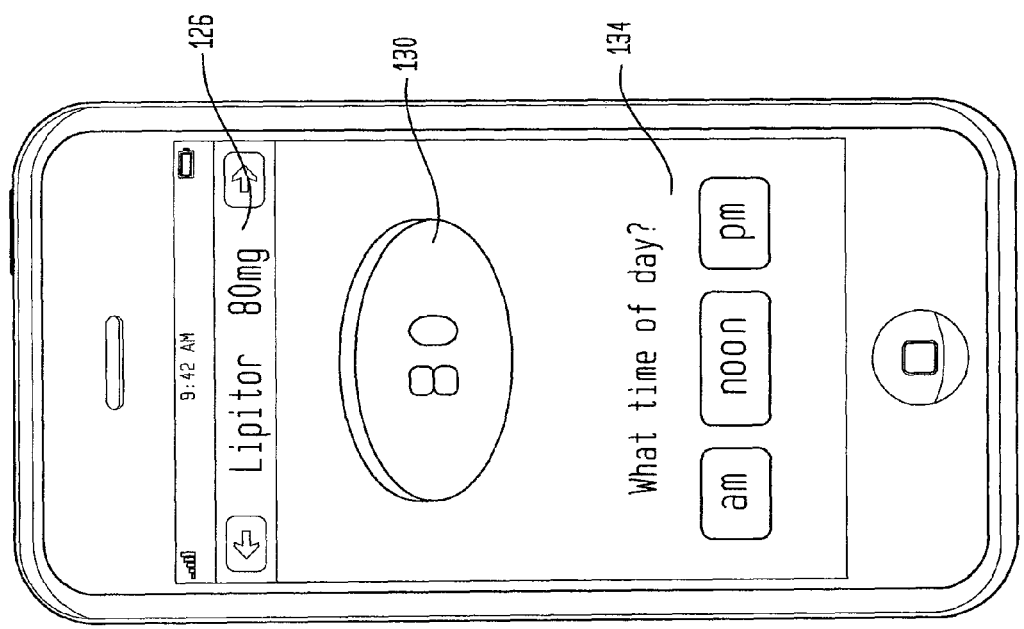
FIG. 14 is an isometric view of a MIWD included in the interactive medicine organizer of FIG. 1 showing a screen for entering first medication special instruction data.

As shown in FIG. 14, the next screen allows the user to enter special instructions 136 such as, for example, "take with food", "do not drink alcohol" or "do not drive or use machinery". These special instructions can act as important safety warnings at the time the medicine is dispensed.

Figure 15:
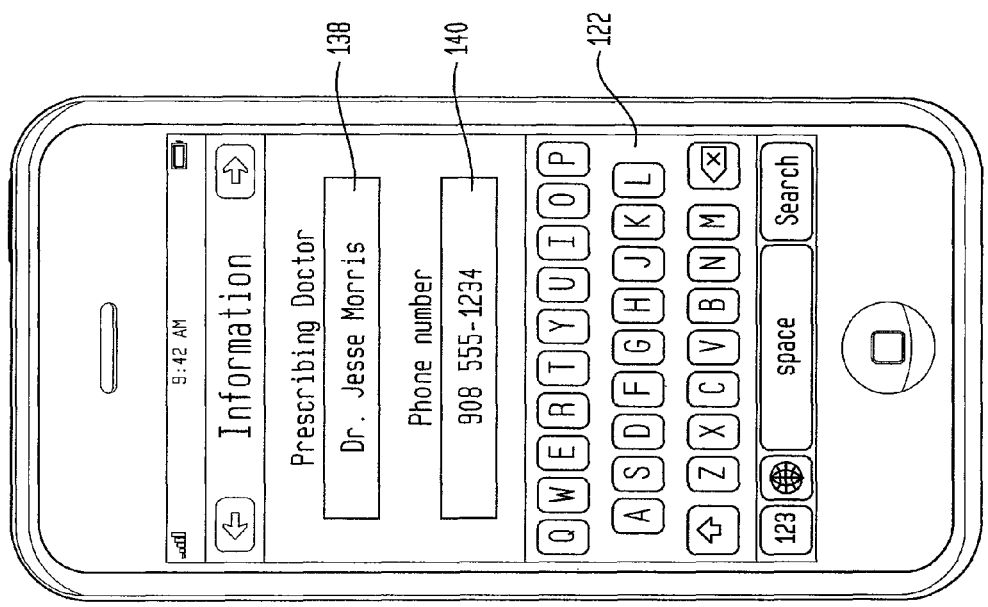
FIG. 15 is an isometric view of a MIWD included in the interactive medicine organizer of FIG. 1 showing a screen for entering prescribing doctor data.
Figure 20:
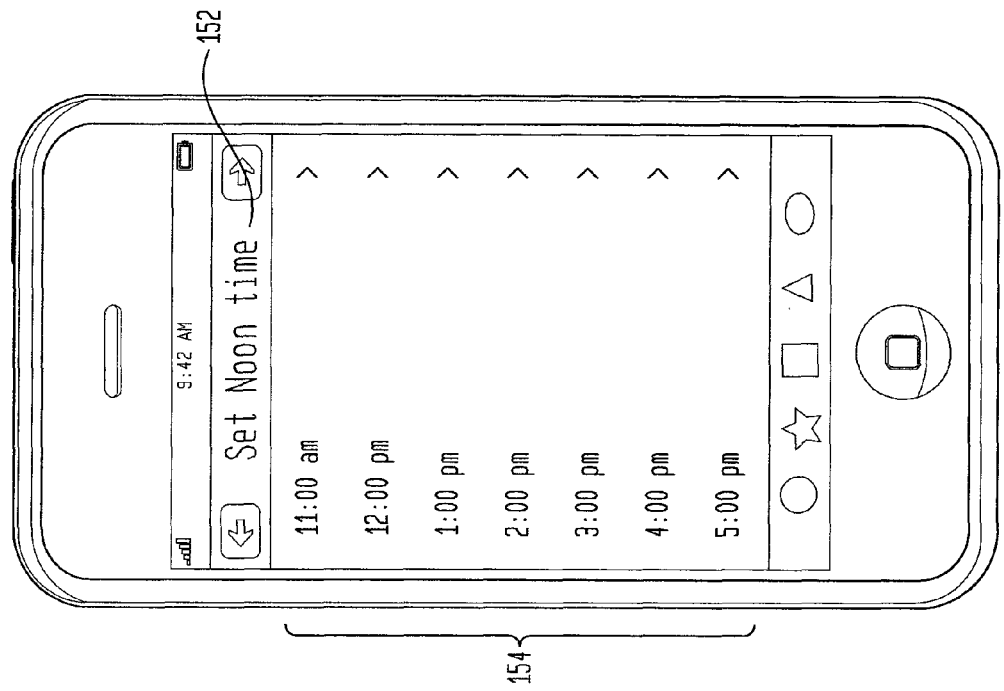
FIG. 20 is an isometric view of a MIWD included in the interactive medicine organizer of FIG. 1 showing a screen for setting a time.
Figure 19:
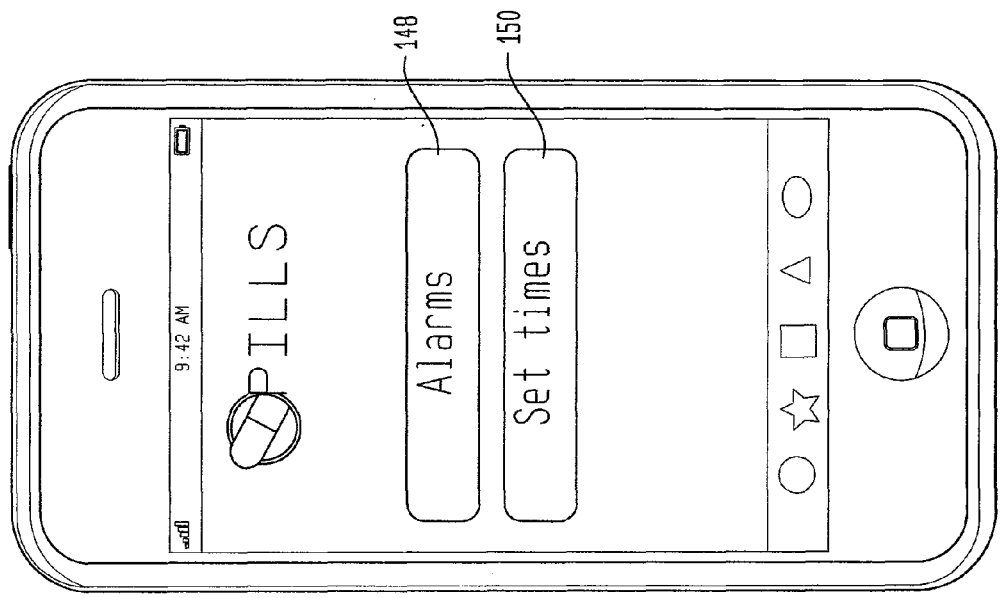
FIG. 19 is an isometric view of a MIWD included in the interactive medicine organizer of FIG. 1 showing a screen for entering time data.

As depicted in FIG. 15, the MIWD 58 can prompt the user to enter the prescribing doctor's or pharmacist's name 138 and phone number 140, if applicable. In the event the user has a question or experiences a problem, for example, a missed dose, the user can instantly place a call to the prescribing doctor or a pharmacist to obtain appropriate instructions.

Figure 16:
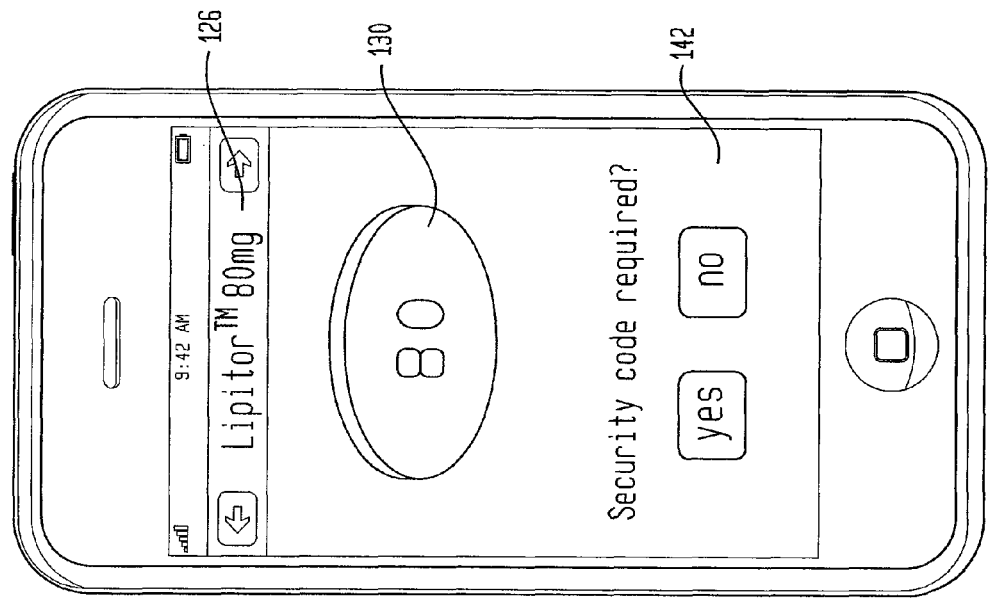
FIG. 16 is an isometric view of a MIWD included in the interactive medicine organizer of FIG. 1 showing a screen for selecting security data.

If desired, the user can enter a security code 142 (FIGS. 16, 17) such that other users may not access or change the user's individual account information, for example, the security code can prevent tampering by young children in the home or prevent a patient from modifying the program to dispense pills at will. This lockout feature can be an important safety feature in preventing unauthorized dispensing off pills or potential overdose.

Next, the user can continue to enter another medication or can begin loading 144 tray 22 (FIG. 18). If "go to next med" 146 is selected, the data entry process is repeated as previously described and depicted in FIGS. 9-17. The process is repeated until all desired medications are entered into the software application database.

Figure 21:
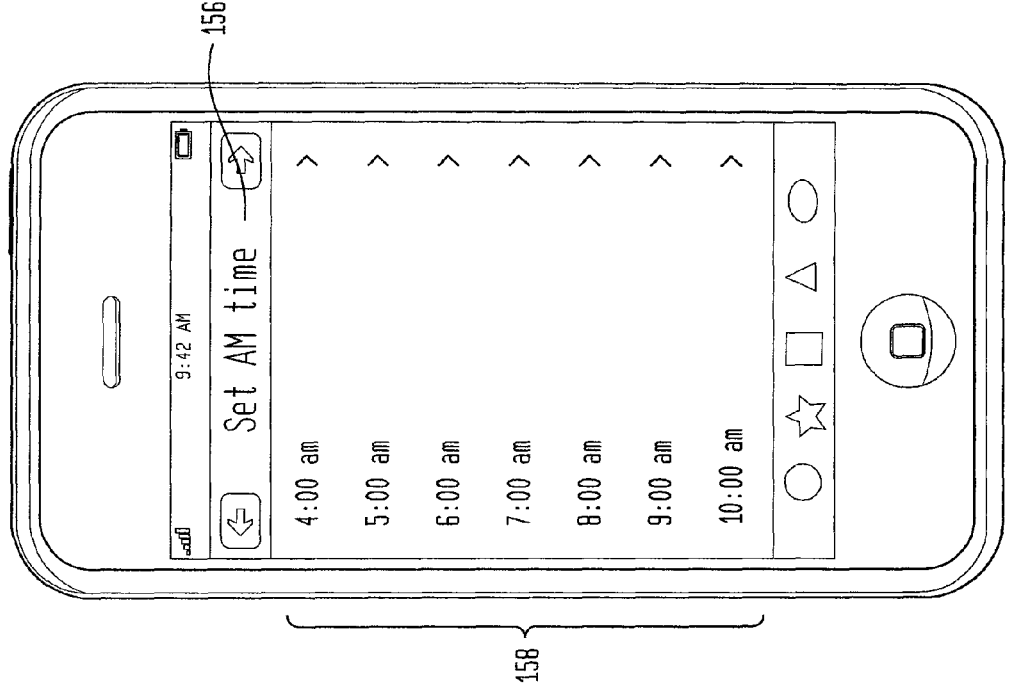
FIG. 21 is an isometric view of a MIWD included in the interactive medicine organizer of FIG. 1 showing a screen for entering alarm data.
Figure 22:
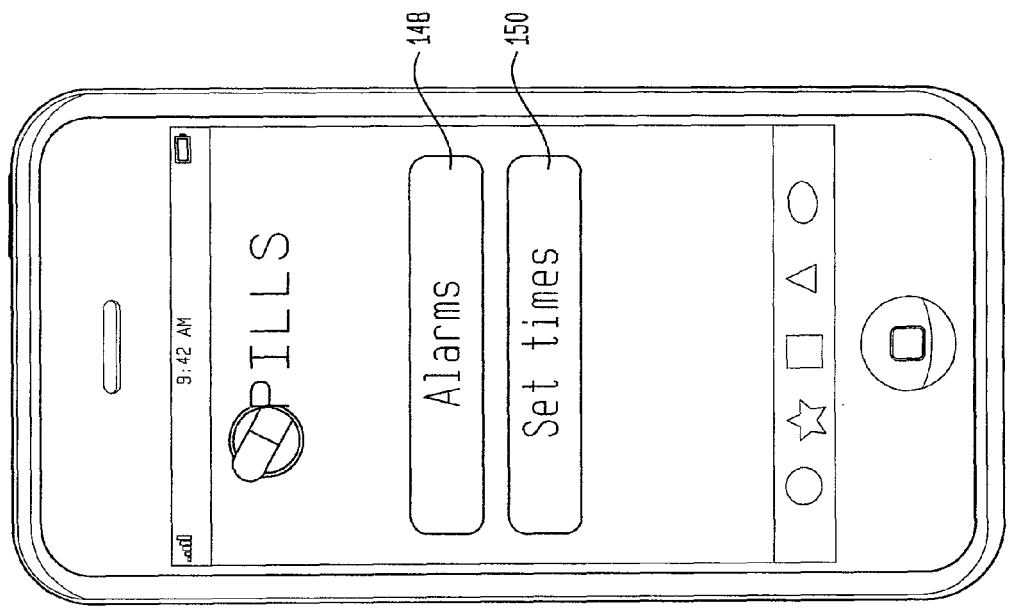
FIG. 22 is an isometric view of a MIWD included in the interactive medicine organizer of FIG. 1 showing a screen for setting an alarm.

Next, as shown in FIGS. 19-22, the application prompts the user to set alarms 148 and times 150 for each time field (AM, NOON, PM) to a specific time. The noon time alarm 152 can be set for any hour and minute 154 as shown, for example, in FIG. 20. Similarly, the AM alarm time (156) can be set to any hour and minute 158 as shown in FIGS. 21-22. The time and alarm fields can be set to any time or any number of times per day.

Loading Example

When the user selects "begin loading" 144, (FIG. 18) the user is guided through the pill loading process. That is, the user can be instructed which pills to place in each compartment for the entire month, if desired. The "Pills" software application can guide the user visually or audibly to load each of compartments 30A, 30B and 30C with the proper pills. The software application causes the MIWD to send an electrical signal to drive the motor 50. The motor 50 rotates the tray 22 and the loading doors 68 to the proper position for each day and each time to ensure accurate loading of each chamber and compartment.

For example, when the user is prompted to load pills into a "Sunday AM" chamber of the tray, the MIWD will display the name and a picture of all medications to be loaded into the "Sunday AM" chamber. The loading doors 68 can be commanded into position such that the user can easily load the specified pills into the correct compartment and chamber (i.e. 30A, 30B, or 30C) of the tray 22. The MIWD has a microprocessor that can electrically commands the movable loading doors 68 to the proper position for each day and time by commanding motor to move the loading door mechanism to the proper position. This feature virtually eliminates the possibility of accidentally placing pills into the wrong compartments or chambers.

When the loading process is complete for "Sunday AM", the IMO will advance tray 22 to the next compartment (30A, 30B, 30C), for example, "Sunday NOON" and will display the name and images of the pills that are to be loaded into the "Sunday NOON" compartment. Again, the movable loading doors 68 are automatically positioned in place above the "Sunday NOON" compartment by interaction of the MIWD which commands the tray 22, the loading doors 68 and the dispensing doors to the proper positions. This process is repeated until all medications are loaded into the appropriate compartments in the tray.

When the tray is loaded a second time, (i.e. the next month, next week), or for all subsequent loading times, the MIWD application can save all loading sequences so that each user or user account, does not need to re-enter the medicine, dose and time information. The user can load the tray without any further programming effort. Further, the user can modify a saved schedule as needed to change any or all parameters. For example, if a user takes the same five medications each day and her doctor adds a new medication, the user can simply add the new medication to the existing schedule which has been saved in the MIWD database and the remote server database. The MIWD database and the server database can be synchronized. The MIWD application is designed to be flexible for ease of use and maximum efficiency.

Medication Time.

After the IMO is programmed and loaded with pills, the MIWD can alert 160 the user when it is time to take the appropriate medication. First, the MIWD can signal the user with a visual or audible alarm 170 or both. The audible alarm can be selected from audio files residing on the MIWD. For example, a ring tone can act as an audible alarm. At the same time, the MIWD screen can display a visual alert 162 comprising the dose time 164, an image of the pill or pills to be taken and their names 166 (FIG. 23).

To dispense the pills, the MIWD can be mated to docking station 60 of the dispenser body 2. The user can press the touch screen display area indicating "DISPENSE" 168 as shown in FIG. 24. A signal from the MIWD positions the dispensing doors, via an electromechanical positioning means such as motor 50, thereby causing the pills in the predetermined compartment to move into dispensing drawer 70. Once the pills are dispensed, the user can slide the drawer out to access the proper pills at the proper time.

As shown in FIGS. 23-24, the MIWD can enter an alert mode 160 when a dose is missed. The MIWD screen can display which medications were missed along with the dose time and images of the missed doses 166. Further, the MIWD application provides useful instructions 163 to the user regarding what to do in the event of a missed dose and provides instant access to the prescribing doctor's phone number. With a touch of the MIWD touch screen, the patient can call the prescribing doctor or dispensing pharmacist for additional advice. The MIWD can also provide internet hyperlinks to the pill manufacturer's website for additional information about each medication, for example, medication side-effects (not shown).

Monitoring and Compliance.

Figure 25:
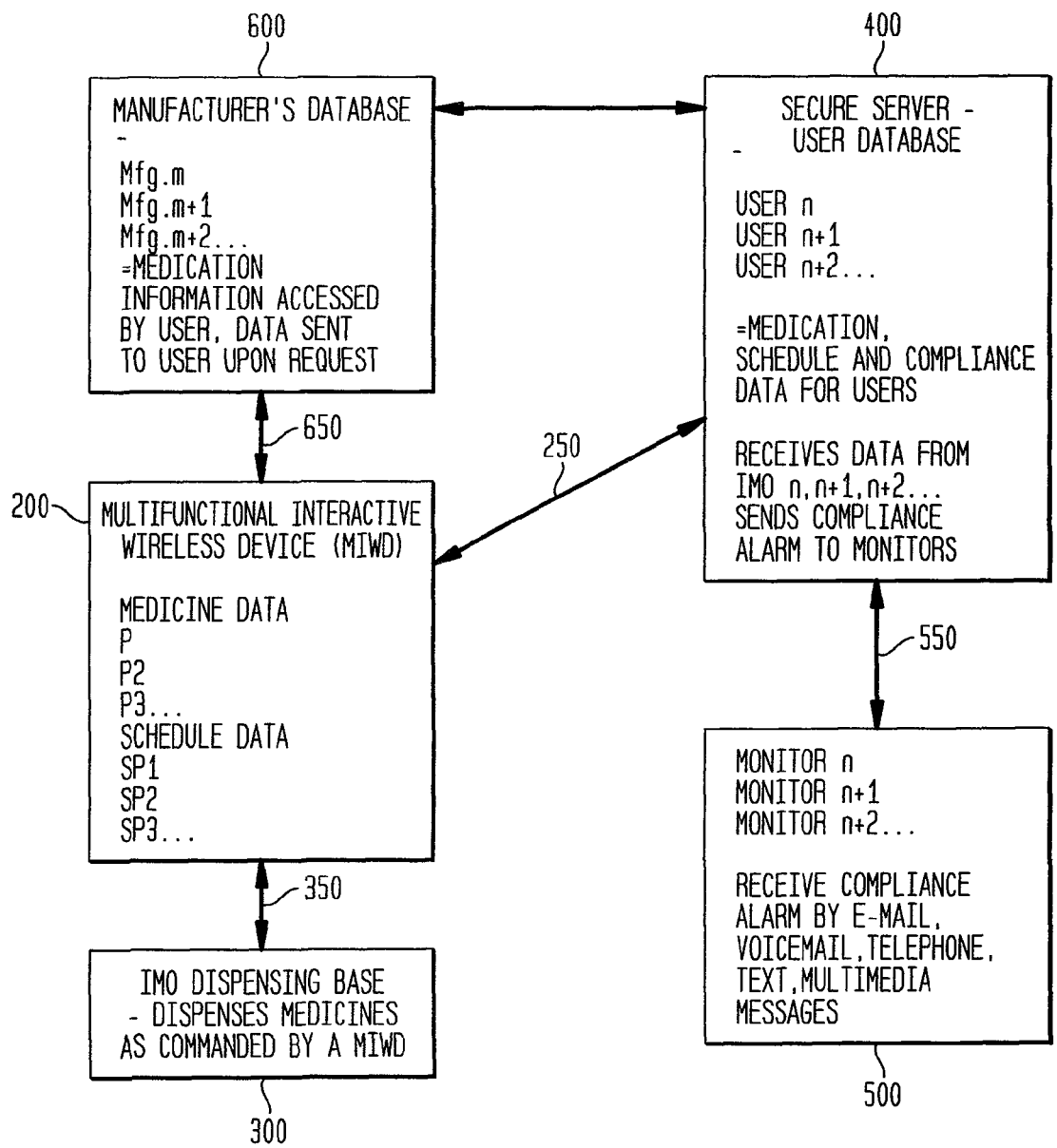
FIG. 25 is a schematic showing some of the system elements included in the interactive medicine organizer of FIG. 1.

As shown in FIG. 25, when a dose of pills, that is, the contents of a compartment is dispensed, a signal 250 is sent from the MIWD application data base 200 via a network to the user's private database 400 on secure server (not shown). The database is maintained on the MIWD 58 (not shown) and on the secure server database 400. The databases can be synchronized. The network can be a cell phone network, a WiFi network or any other type of wireless or wired network with internet connectivity. In one embodiment, the application can include the ability to communicate through a hard line network such as a cable network or fiber optics network to connect to the internet.

As discussed above, dispensing data can be communicated to the remote server database 400; the data is available for review and analysis by the user or a care taker. The data may be presented in any number of ways including charts, graphs or tables. In this way, the user's medication dispensing history can be reviewed for compliance with the desired schedule for taking the medications.

In one embodiment, the application includes a feature which alerts a care taker that a dose has not been dispensed via a signal 550 to the network. For example, application can generate a message 500 such as phone message, text message or e-mail message which can be sent directly to the user, care taker, doctor, family member or any number of interested parties. This feature can be particularly useful when, for example, a care taker or family member desires to monitor the medication dispensing compliance of a senior citizen such as a parent, family member or individual who may be suffering from a memory disorder or who may simply be forgetful. When the user receives a "missed dose" message, appropriate action can be taken in real-time to correct the short term non-compliance and address the longer term issues associated with the inability or unwillingness of a patient to comply with a medication schedule. This process is described in more detail below. Further, a similar alert can be sent when a user attempts to dispense pills too often or in a manner inconsistent with the proper medication schedule.

As illustrated above, users can input data for numerous medications into the databases 200, 400. Medication specific supplementary information can also be provided directly by a network link 650 from a manufacturer's database 600 for one or more medications. Supplementary information can include, for example, the name of the medication, its function, how and when the medication should be taken, missed dose information, information about side effects including specific actions required if the patient experiences side effects, possible interactions with other medications, and where the patient can find additional information about the medication, such as hyperlinks to the manufacturer's website. Further, manufacturers can send coupons and other desirable information such as, for example, safety alerts directly to users through the network to the IMO.

Referring to FIG. 25, the MIWD comprises a software application (app) that is programmed to store medicine and schedule data for one or more medications. The MIWD database 200 stores medicine and schedule information that is input by the user or acquired from the manufacture's database 600. The MIWD database 200 can be used to command the IMO dispensing base 300 to one or more loading positions and one or more dispensing positions by a wireless signal 350 or by a hard line electrical signal 350, for example, by docking the MIWD 58 with the docking station 60. When a dose is dispensed or missed by the user, the MIWD communicates with the secure server database 400. Server database 400 can be accessed by users having a password and a username. Authorized users can login to the database 400 to monitor patient compliance.

It is contemplated that numerous graphs and reports can be displayed or printed such that the person accessing the database 400 can easily recognize compliance problems, determine whether there are any recurring compliance problems, or print medication lists.

As previously described, database 400 can communicate with monitoring module 500. In the event of a compliance problem, for example, a missed dose of heart medication, module 500 can issue commands to send an alarm or alarms to concerned individuals by e-mail, text or other means. In this way, a care taker can be timely notified of a missed dose and can implement corrective action.

As will also be appreciated, a significant benefit of the present invention includes the ability to store the user's medicine schedule on both an MIWD that the user may carry with them and on a secure online database. A patient's medication information can be invaluable to a new doctor or in the event a user is taken to the hospital. The present invention allows a nurse, doctor, EMT or other health care professional to access a patient's medication regimen or dispensing history by accessing the server database. This feature can dramatically reduce the risk of prescribing the wrong medication and also reduce the time before necessary treatment is administered.

Figure 26:
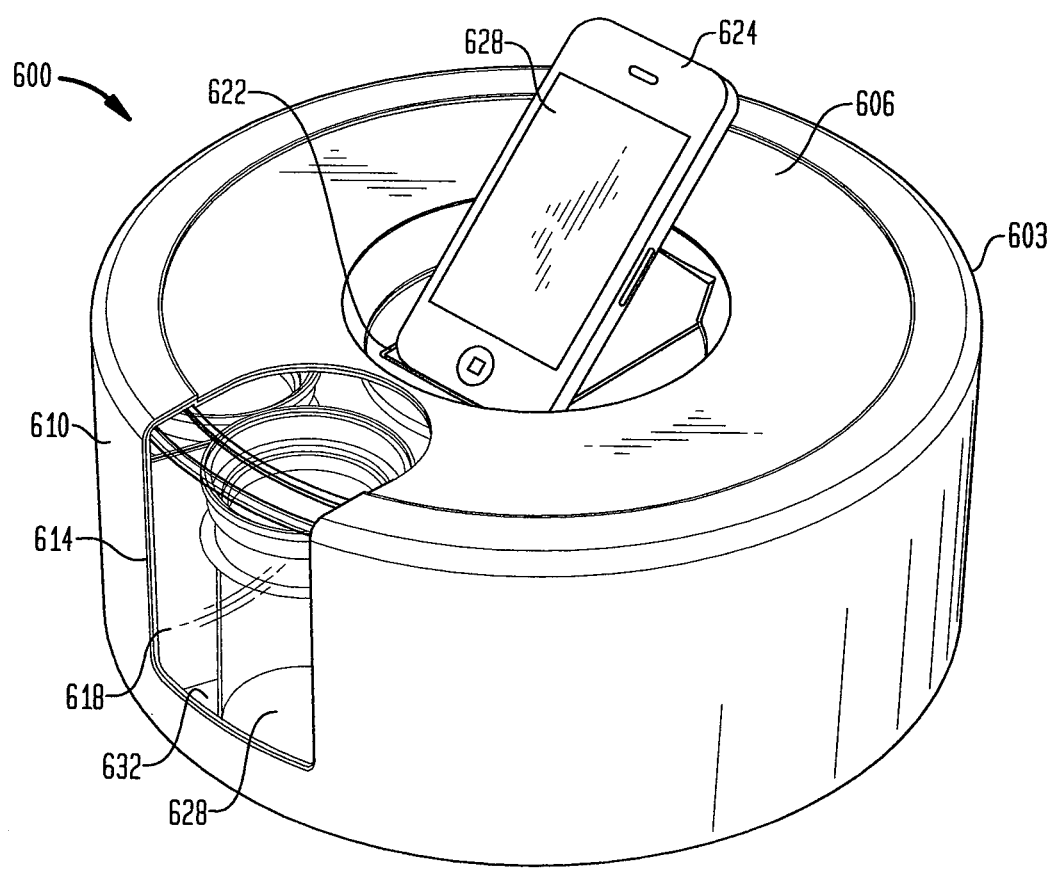
FIG. 26 is a perspective view of an interactive medicine organizer according to one embodiment of the present invention in a closed position.

FIG. 26 depicts another aspect of the present invention. As shown, interactive medicine organizer (IMO) 600 in accordance with one embodiment of the present invention includes a housing 603. Housing 603 has a top surface 606, side surface 610 and bottom surface (not shown). Housing 603 has an aperture 614 for accommodating loading and unloading door 618. Housing 603 also includes docking station 622 for docking with MIWD 624 which is substantially similar to the docking interface as described above.

FIG. 26 depicts IMO 600 in a closed position, that is, the door 618 is closed and locked such the medicine vial 628 that is loaded on rotatably mounted tray 632 cannot be accessed without authorization.

The housing, door and other internal components similar to those discussed above can be fabricated from engineering polymers or other structural materials which will be known to one skilled in the art of manufacturing. In some embodiments, the housing or door can be made from a transparent or translucent material. If desired, a clock can be mounted to the housing as described above.

Figure 27:
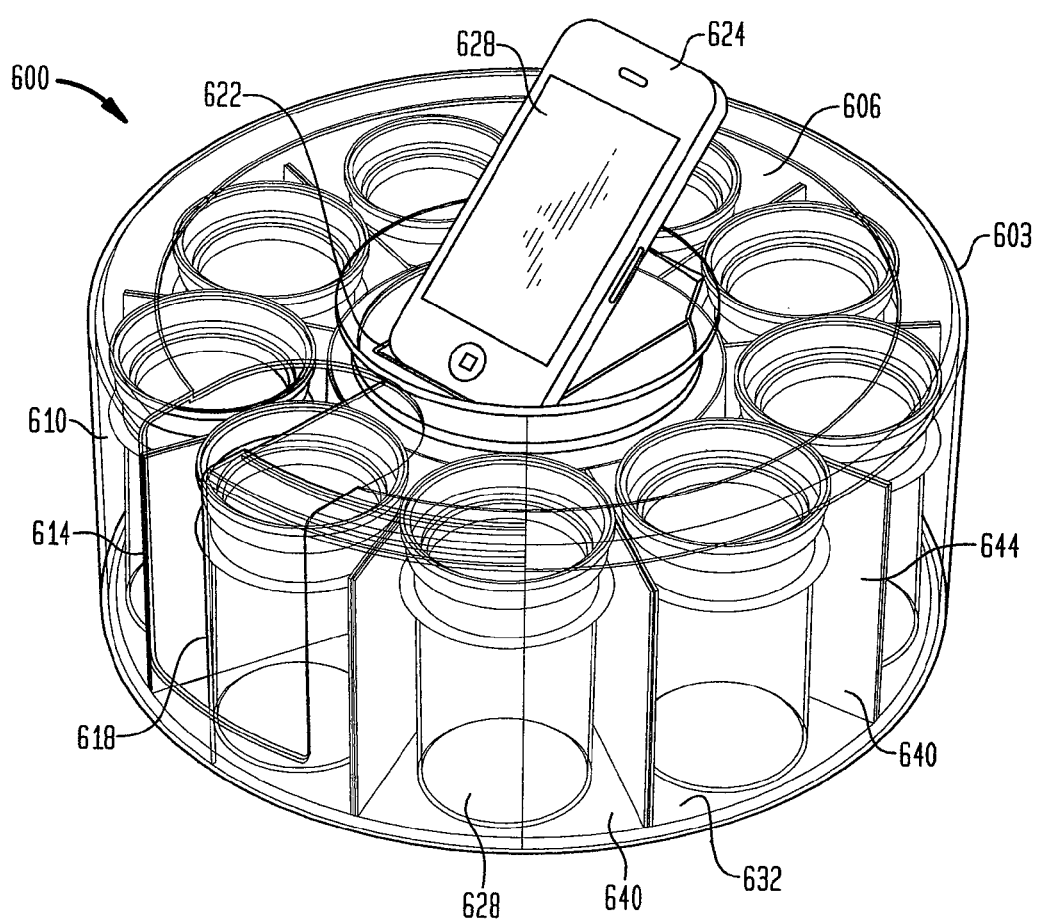
FIG. 27 is a perspective view of an interactive medicine organizer according to one embodiment of the present invention in a transitory position.

As shown in FIG. 27, in this embodiment, tray 623 is rotatably mounted within housing 603. Tray 632 is circularly shaped and comprises nine (9) chambers 640, each having a wall 644 between them. Each chamber is capable of storing a medicine vial or container, such as, for example vial 628. Although nine (9) vials are shown in this embodiment, as discussed above, a wide variation of tray geometries, chamber configurations, and compartment configurations are contemplated to be within the scope of the present invention.

To facilitate loading, the chambers can be color coded, for example, to indicate a first color for a morning dose, a second color for an afternoon dose and a third color for an evening dose. Tray 632 and walls 644 can be molded or fabricated from any suitable durable structural material, for example, a polymeric material. Suitable materials and manufacturing methods will be well known to those skilled in the art.

In this particular embodiment, tray 632 is designed to hold a nine (9) medicine vials. In this way, up to nine medications are available for a medicine taker or user of the organizer. Each chamber can hold a vial and each vial can hold a pre-determine number of pills or doses. For example, a one month supply or a three month supply of medicine can be stored in each vial. As discussed above, the compartments can be configured to hold a plurality of geometries and types of medicine delivery systems, such as, for example, asthma inhalers or nasal sprays.

As shown in FIG. 27, door 618 can be commanded to an open or a closed position. FIG. 27 depicts an intermediate transitory position in which the door can be opened to allow for loading or dispensing or closed to facilitate loading of another chamber or a closed, ready to dispense position. As discussed above, the door can be commanded to an open or a closed position.

Figure 28:
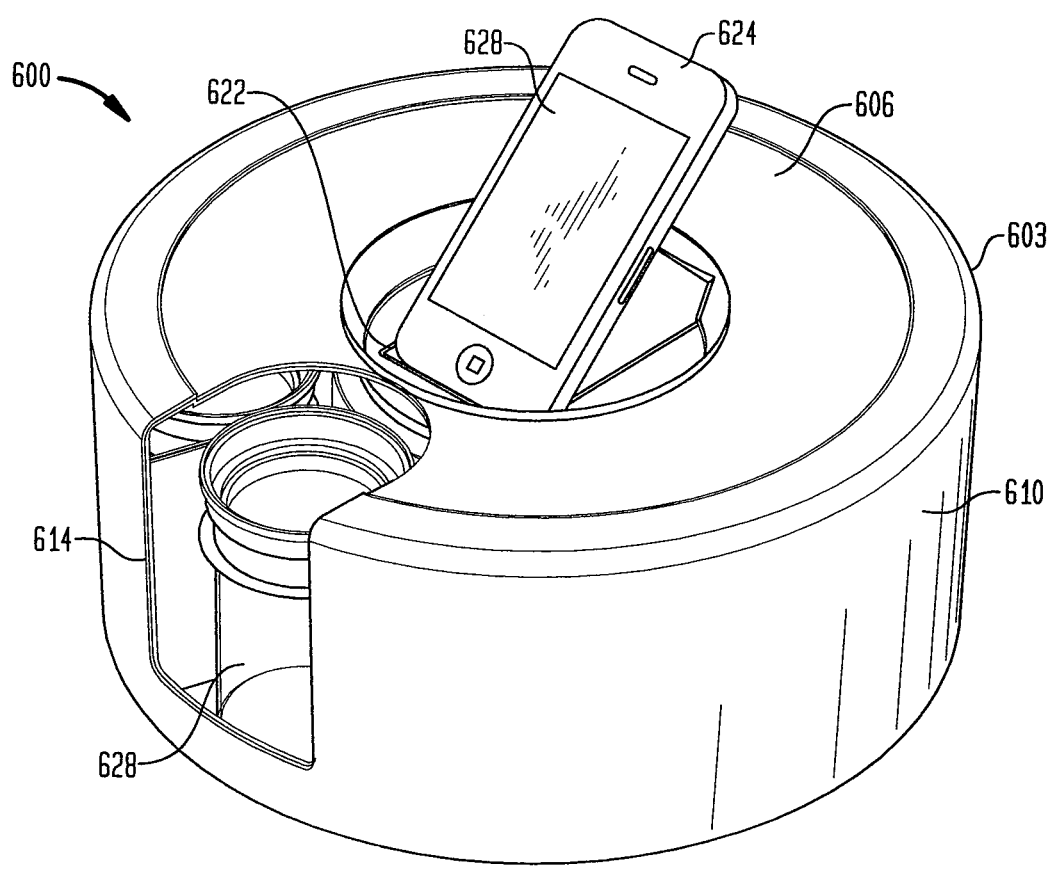
FIG. 28 is a perspective view of an interactive medicine organizer according to one embodiment of the present invention in an open loading or dispensing position.

As shown in FIGS. 26-28, the tray has nine chambers or compartments 640. Each compartment can be identified by the organizer and synchronized such that the MIWD recognizes which medicine is in which compartment. In some embodiments, the organizer can include a bar code scanner for identification and verification of each medicine and its location within the IMO.

As discussed above, tray 632 is indexed and controlled by electric motor (not shown). The motor is mechanically connected to tray 632 and electrically connected to an AC power source. The motor is commanded by electrical signals generated by a microprocessor in multifunctional interactive wireless device (MIWD) 624. An MIWD can be, for example, an iPhone™, a BlackBerry™, a Centro™, a PDA, an iPod™, a Droid™, an iPad™ or any similar touch or smart wireless device or smart phone device. Standard motors, such as precision stepper motors, which are known to those of ordinary skill in the art can be utilized to accomplish the movement of any mechanism in the IMO that requires control or movement.

IMO 600 can include a battery backup system to maintain power in the event of an AC power interruption. If power is lost, all data can be stored in memory on MIWD 624 which can also be synchronized with a website on a remote server.

As discussed, IMO 600 includes docking station 622. In this embodiment, docking station 622 is integrated to top surface 606 of housing 603. Docking station 622 is adapted to accept and connect with MIWD 624. Docking station 622 provides mechanical means to support the MIWD such that pressing on a touch screen 628 incorporated in the MIWD will not damage the IMO and will facilitate durable mechanical and electrical connectivity between the MIWD and the dispenser body. The MIWD mates with the docking station such that the MIWD may be electrically charged or recharged through the AC power source or battery. Other means and locations to connect the MIWD and the IMO, such as, for example, an adapter cord between the MIWD and the IMO are contemplated.

It will be appreciated that in certain embodiments, docking station 622 can comprise a wireless receiver that receives signals from the MIWD or other wireless device. Any wireless interface that can send and receive signals to and from the MIWD is contemplated. In such embodiments, physical docking of the MIWD may not be necessary.

When the MIWD is mated to the IMO through the docking station, the MIWD can send commands to cause the electric motor or the door to move. Further, the MIWD can receive signals from the motor in order to recognize the position of tray within the body such that the position of each chamber can be commanded to any position. Thus the IMO can be programmed to load or unload a medicine into or out of any chamber at any time. It will be understood that the docking station can include any number of adapters such that different types of MIWD can be docked. Such docking adapters and command and control algorithms between electromechanical devices are well known to those of ordinary skill in the art.

Dispenser housing 603 incorporates movable loading door 618 for loading medicine or medicine containers into the chambers 640. As shown in FIGS. 26-28, loading door 618 can be commanded by the MIWD to an open position (FIG. 28) for loading each chamber.

Loading door 618 can be commanded to a closed position, as shown in FIG. 26, or an open position, as shown in FIG. 28, in order to protect the contents of the compartments and to ensure that only the desired compartment is loaded or unloaded. The loading door is closed when the IMO is not being loaded. The loading door can be made of a transparent material such that the contents of the compartments aligned with the loading doors are visible to the user. The loading door configuration can include other commandable mechanisms such as, for example, a rotating member having apertures spaced to facilitate an open position in which at least one compartment can be loaded or a closed position in which all compartments are closed and cannot be loaded. Configurations having any number of doors for loading and unloading the IMO are contemplated.

In this embodiment, the IMO comprises a loading door that underlies the housing. The door can be connected to the housing by a hinge or other slideable mechanism. In operation, the loading door can be commanded by the MIWD to an open position to expose each chamber for loading or unloading medicine. The door can also be commanded a closed or locked position.

Movement of the door is accomplished by electrical or wireless commands sent from a software application resident on the MIWD. Door movement can be accomplished by any suitable mechanical system such as a motor and actuator configured to move one or more doors to a desired position. Such methods for command and control that may be used for opening and closing the door will be well known to a person of ordinary skill in the electro-mechanical arts. Any suitable mechanism is contemplated herein. Further, it is contemplated that that one or more doors can be commanded open or closed remotely or wirelessly.

In operation, the IMO 600 is controlled by a software application executed by MIWD 624. In this embodiment, the MIWD is an iPhone™, but any mobile phone or wireless device capable of running third party applications and controlling hardware can also be used. The MIWD 624 can also maintain a wireless internet connection such as, for example, 3G, 4G, satellite, wireless or WiFi technology that allows for connection to the internet. The wireless connection permits, among other things, remote monitoring of a user defined medicine schedule and monitoring compliance with the schedule.

Figure 29:
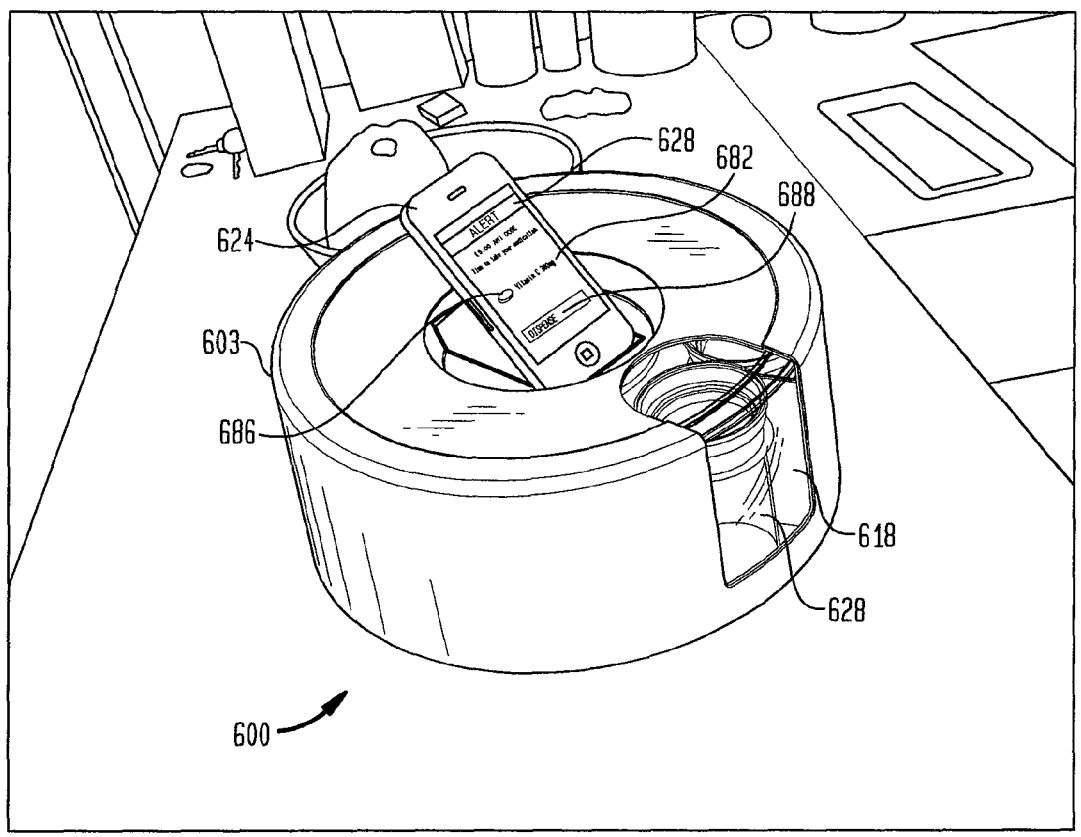
FIG. 29 is a perspective view of an interactive medicine organizer according to one embodiment of the present invention in a closed position.

As shown in FIG. 29, the user interface on the MIWD can have a graphical display designed for ease of use. The user can be guided through a series of steps to set up and program the IMO, dispense pills and perform other desirable functions.

After the organizer is programmed and loaded, it will prompt a user to take their medications according to the schedule input. For example, at 9:00 am, it is time to take medicine A (500 mg of vitamin C) and a morning dose of medicine B. The MIWD display 628 can show a picture or icon of medicine A 686 and medicine B (not shown) using a touch screen dispense button 688 located next to the medicine prompt. When the user docks the MIWD with the docking station and presses the button 688 to dispense medicine A, the tray rotates to the compartment holding medicine A and opens the door. The user removes the container holding medicine A, removes the appropriate dosage and returns the medicine container back in the chamber or compartment. The user then presses a "done" button on the MIWD display. The same procedure can be repeated for other medicine per a user defined schedule.

In this embodiment, each compartment can have a sensor to indicate whether or not the chamber contains a medicine container. Such sensors will be known to those of ordinary skill in the art of electronic sensors.

When a sensor indicates that the user has replaced medicine A, the door closes. The MIWD display will then show a picture of medicine B with a dispense button as discussed above. When the user presses the dispense button, the tray rotates to the chamber or compartment containing medicine B and opens the door.

The user removes the container holding medicine B, removes the appropriate dosage and returns the container to the open compartment. The user then presses a "done" button on the MIWD display. The IMO software application can record that the user's morning dose has been dispensed and can send a signal to a website on a remote server. The website can be accessed by one or more authorized users, who can track the dispensing history or compliance with a medication schedule of one or more particular users.

Figure 30:
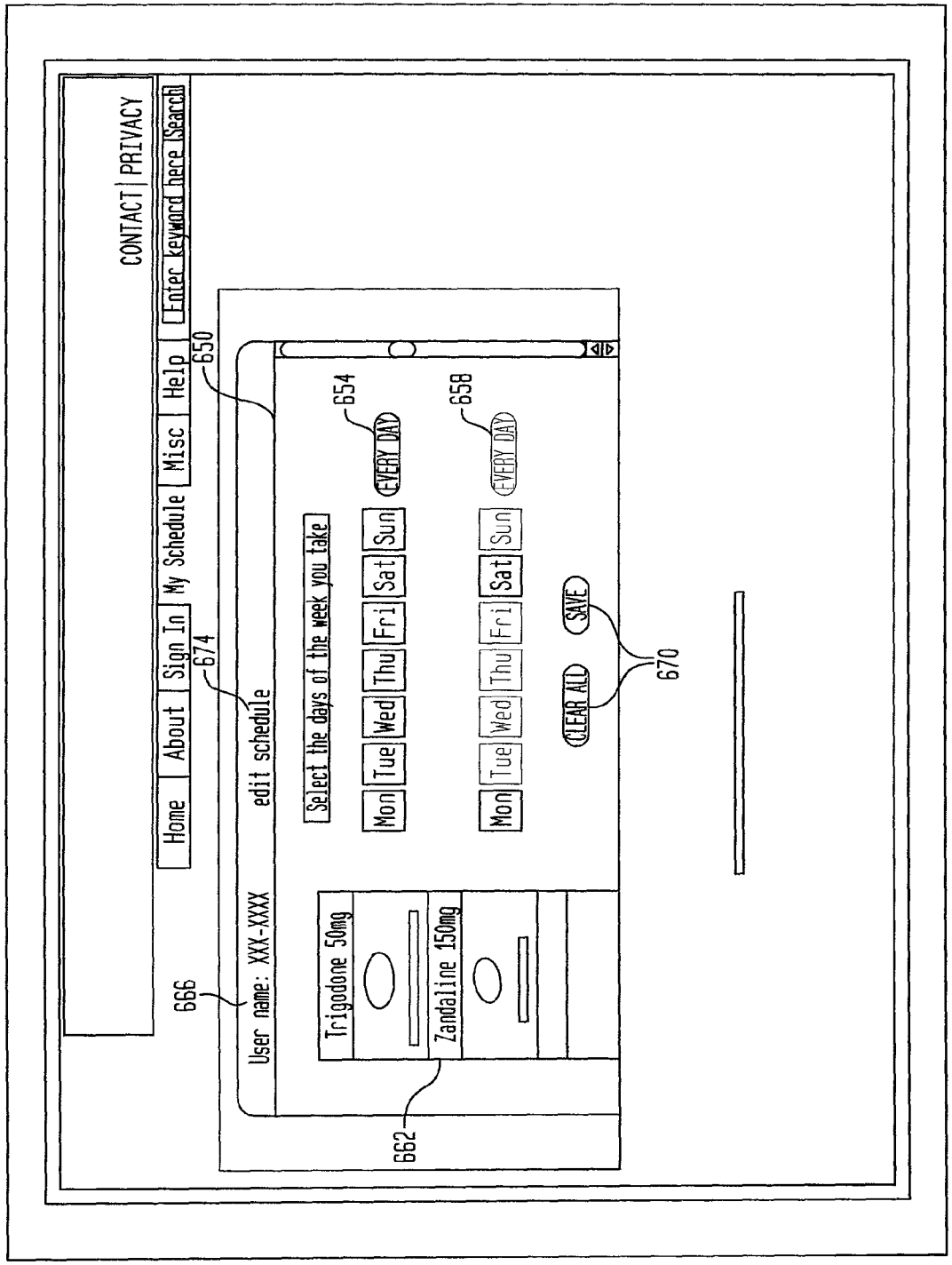
FIG. 30 is a schematic view of a web interface according to one embodiment of the present invention.

As shown in FIG. 30, the website can also include a user interface for programming the device. In this embodiment, the user interface screen 650 can include, for example, icons for each day of the week or for every day 654, icons for each day or every day 658, icons for selecting one or more medications and the schedule associated with each medication 662, a user name 666, and a clear or save icon 670. Clicking on the "edit schedule" icon 674, allows the user to enter an editing mode to input medicine schedule data.

In addition to keeping track of one or more user's medication schedule and dispensing history, the IMO can be used to prevent unauthorized use of medications. For example, the application running on the MIWD can include a lock-out feature which requires the user to perform an unlocking operation, such as entry of a numeric code, before the organized will dispense medication. The unlock code can include alphabetic characters, numeric characters, symbols, pictures and combinations thereof. The lock-out feature can also include a set number of errors, that is when the wrong code is entered, that will generate an administrative signal and lock the device until the device can be reset by an authorized administrator.

In one embodiment of the invention, the medicine dosing schedule can be separated by the specific medication to be loaded. For example, User A must take medicine A twice a day, once in the morning and once in the evening. User A also must take also medicine B once in the morning and medicine C once in the evening.

Once programmed as discussed above, the MIWD will alert or signal User A to load medicine A and open the door so that User A can load medicine vial A into the open chamber or compartment. The MIWD can also request and store information about how many pills are in vial A at the time of loading so that the number of pills dispensed can be tracked and a prescription renewal reminder can be generated when a preset number of pills are dispensed or remain in the vial.

Next, the MIWD signals the door to close and causes rotation of the tray to a predetermined open space so that medicine vials B and C can be loaded.

It is contemplated that a plurality of medications and medicine vial geometries fall within the scope of the present invention. For example, the tray can have thirty (30) compartments wherein each compartment can accommodate a two inch diameter, four inch high, circular shaped vial. Such medicine dispensing vials and their various geometries will be known to those of ordinary skill in the medicine dispensing arts.

In another aspect of the present invention a user enters a medicine schedule. The schedule can be entered via a secure website as discussed above or directly on a MIWD such as smart phone, for example an iPhone™ or Droid™ The MIWD is docked to the device through the docking station. The MIWD can be synchronized with the website via any type of wireless or cell phone network.

Although the invention herein has been described with reference to particular embodiments, it is to be understood that these embodiments are merely illustrative embodiments and that other arrangements may be devised without departing from the spirit and scope of the present invention as defined by the disclosure herein.

What is claimed is:

1. An apparatus comprising:
   (a) a dispenser body having a housing;
   (b) a commandable lockable slidable door, said door being slidably connected to said housing to allow a user access to items stored within said housing;
   (c) a commandable rotating tray, said tray having one or more chambers, said tray being mounted within said housing and forming an integral component of said housing;
   (d) a docking station, said docking station being connected to said housing; and
   (e) a multifunctional interactive wireless device, said device being capable of i) docking with said docking station, ii) commanding said tray to a plurality of positions, iii) commanding said door to slide between a plurality of locked or unlocked positions, wherein said device executes a software application for determining said plurality of positions of said tray, and said door based on a data set input by a user, and said commanding is performed by physical docking of said multifunctional interactive wireless device with said docking station or wirelessly without physical docking of said multifunctional interactive wireless device with said docking station.

2. The apparatus of claim 1, wherein said tray is substantially circular.

3. The apparatus of claim 2, wherein said tray comprises nine chambers.

4. The apparatus of claim 3, wherein each of said nine chambers is configured to accept a medicine vial.

5. The apparatus of claim 1, wherein said multifunctional interactive wireless device is a smart phone.

6. The apparatus of claim 1, wherein said multifunctional interactive wireless device is a smart tablet.

7. The apparatus of claim 1, wherein said data set comprises:
   (a) a name of a medicine;
   (b) a strength of said medicine; and
   (c) a time schedule for dispensing said medicine.

8. The apparatus of claim 1, wherein said multifunctional interactive wireless device communicates a signal to a remote database, said signal indicating a dispensing history.

9. A method comprising:
   (a) entering a data set into a software application, said application being executed on a multifunctional interactive wireless device;
   (b) docking said multifunctional interactive wireless device with a docking station;
   (c) using said multifunctional interactive wireless device to command a lockable slidable dispensing door to slide from a closed locked position to an open loading position to allow a user access to items stored within said housing;
   (d) loading one or more medicine containers into a commandable rotating tray, said tray having one or more chambers, said tray being mounted within said housing and forming an integral component of said housing;
   (e) using said multifunctional interactive wireless device to command said dispensing door to slide from an open unlocked position to a closed locked position to prevent access to items stored within said housing;
   (f) receiving an alert from said multifunctional interactive wireless device at a predetermined time indicating to the user that it is time to take the appropriate medication;
   (g) docking said multifunctional interactive wireless device with said docking station;
   (h) using said multifunctional interactive wireless device to command said dispensing door to slide from a closed locked position to an open loading position to allow a user access to items stored within said housing;
   (i) unloading said one or more medicine containers from said commandable rotating tray.

10. The method of claim 9, wherein said data set comprises:
    (a) a name of one of more medicines;
    (b) a strength of said one or more medicines; and
    (c) a time that said one or more medicines is to be dispensed.

11. The method of claim 9, further comprising the step of transmitting a signal from said multifunctional interactive wireless device to a remote database, said signal indicating either a confirmation of dispensing said one or more medicines or a failure to dispense said one or more medicines.

12. The method of claim 9, further comprising the step of transmitting one or more alarms from said multifunctional interactive wireless device when said one or more medicines are not dispensed within a predetermined time of a scheduled dispense time.

13. The method of claim 9, wherein said multifunctional interactive wireless device is a smart device.

14. The method of claim 11, further comprising the step of:
    (i) sending a signal to said remote database when a user attempts to dispense said one or more medicines before a predetermined time.

15. The method of claim 11, further comprising the step of:
    (j) sending a signal to said remote database when a user attempts to dispense said one or more medicines more than a predetermined number of times.

16. The method of claim 9 further comprising the step of:
    (k) locking said dispensing door when a user attempts to dispense said one or more pills before a predetermined time.

17. A method comprising:
    (a) loading a pre-loaded medicine container containing medication into a commandable rotating tray, said tray being enclosed in a housing having a slidable lockable door, said tray having one or more chambers and forming an integral component of said housing;
    (b) using a multifunctional interactive wireless device to command said slidable lockable door to slide from a closed locked position to an open loading position to allow a user access to items stored within said housing;
    (c) receiving an alert from said multifunctional interactive wireless device at a predetermined time indicating to the user that it is time to take the appropriate medication;
    (d) using said multifunctional interactive wireless device to command said slidable lockable door to slide from a closed locked position to an open loading position to allow a user access to items stored within said housing;
    (e) unloading said medicine container from said tray, wherein a user can access said medication and reload said container into said tray.

18. The method of claim 17, wherein said commanding is performed using a wireless signal originating from said multifunctional interactive wireless device.

19. The method of claim 17, wherein said multifunctional interactive wireless device is a phone.

20. The method of claim 17, wherein said multifunctional interactive wireless device is a smart device.

\* \* \* \* \*